United States Patent
Ioffe et al.

(10) Patent No.: US 10,532,096 B2
(45) Date of Patent: *Jan. 14, 2020

(54) METHODS AND COMPOSITIONS COMPRISING A COMBINATION OF A VEGF ANTAGONIST AND AN ANTI-CTLA-4 ANTIBODY

(71) Applicant: REGENERON PHARMACEUTICALS, INC., Tarrytown, NY (US)

(72) Inventors: Ella Ioffe, Bronx, NY (US); Israel Lowy, Dobbs Ferry, NY (US); Gavin Thurston, Briafcliff Manor, NY (US); Elena Burova, Mount Kisco, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/959,595

(22) Filed: Apr. 23, 2018

(65) Prior Publication Data

US 2018/0236070 A1     Aug. 23, 2018

Related U.S. Application Data

(62) Division of application No. 15/026,460, filed as application No. PCT/US2014/061071 on Oct. 17, 2014, now Pat. No. 9,968,674.

(60) Provisional application No. 61/892,601, filed on Oct. 18, 2013, provisional application No. 61/901,596, filed on Nov. 8, 2013, provisional application No. 61/952,923, filed on Mar. 14, 2014, provisional application No. 62/055,734, filed on Sep. 26, 2014.

(51) Int. Cl.
| | |
|---|---|
| *A61K 39/395* | (2006.01) |
| *A61K 38/17* | (2006.01) |
| *C07K 16/28* | (2006.01) |
| *A61K 9/00* | (2006.01) |
| *C07K 14/71* | (2006.01) |
| *C07K 16/22* | (2006.01) |
| *A61K 39/00* | (2006.01) |

(52) U.S. Cl.
CPC ........ *A61K 39/3955* (2013.01); *A61K 9/0019* (2013.01); *A61K 38/179* (2013.01); *A61K 38/1793* (2013.01); *A61K 39/39558* (2013.01); *C07K 14/71* (2013.01); *C07K 16/22* (2013.01); *C07K 16/2818* (2013.01); *C07K 16/2863* (2013.01); *A61K 2039/505* (2013.01); *A61K 2039/507* (2013.01); *C07K 2317/76* (2013.01); *C07K 2319/30* (2013.01)

(58) Field of Classification Search
None
See application file for complete search history.

(56) References Cited

FOREIGN PATENT DOCUMENTS

| WO | WO 2009937398 A1 | 7/1999 |
| WO | WO 2007/113648 | 10/2007 |

OTHER PUBLICATIONS

Hodi et al., "Bevacizumab plus Ipilimumab in Patients with Metastatic Melanoma" Cancer Immunol. Res. (Jul. 2014) 2(7):632-642.
Kantarijian et al., "Cancer Drugs in the United States: Justum Pretium—The Just Price" Journal of Clinical Oncology (Oct. 1, 2013) 31(28):3600-3604.
Wang, Tzu-Fei and Lockhart, Albert Craig, "Aflibercept in the Treatment of Metastatic Colorectal Cancer" Clinical Medicine Insights: Oncology (2012) pp. 19-30.
Hodi et al., "A Phase I trial of ipilimumab plus bevacizumab in patients with unresectable stage III or stave IV melanoma" Journal of Clinical Oncology, 2011, vol. 29 No. 15, Suppl. 1, No. 8511.
Holash et al., "VEGF-Trap: A VEGF blocker with potent antitumor effects" PNAS, Aug. 20, 2002, vol. 99, No. 17, pp. 11393-11398.
Lockhart et al., "Aflibercept in the Treatment of Metastatic Colorectal Cancer" Clinical Medicine Insights: Oncology 2012:6, pp. 19-30.
Minor et al., "Concurrent bevacizumab (BEV) with biochemotherapy (BC) followed by ipilimumab for advanced melanoma: A phase I-II trial" Journal of Clinical Oncology 2013, May 10, vol. 31, No. 15, Suppl. 1, e20001.
Selby et al., "Anti-CTLA-4 Antibodies of IgG2a Isotype Enhance Antitumor Activity through Reduction of Intratumoral Regulatory T Cells" Cancer Immunol Res; 1(1) Jul. 2013.

*Primary Examiner* — Christine J Saoud
*Assistant Examiner* — Jon M Lockard
(74) *Attorney, Agent, or Firm* — Lisa Dornbach Flanagan; Frank R. Cottingham; Karl Bozicevic

(57) ABSTRACT

The present invention provides pharmaceutical compositions comprising a VEGF antagonist and an anti-CTLA-4 antibody, and methods of use thereof. The compositions and methods of the present invention are useful for the treatment of cancers and other diseases and disorders in which anti-angiogenic therapies and/or targeted immune responses may be beneficial.

32 Claims, 34 Drawing Sheets

Specification includes a Sequence Listing.

METHODS AND COMPOSITIONS COMPRISING A COMBINATION OF A VEGF ANTAGONIST AND AN ANTI-CTLA-4 ANTIBODY

This application is a divisional application of U.S. application Ser. No. 15/026,460, filed Mar. 31, 2016, which issued on May 15, 2018 as U.S. Pat. No. 9,968,674, which application claims priority to U.S. Provisional Application Ser. No. 61/892,601 filed Oct. 18, 2013, which claims priority of U.S. Provisional Application Ser. No. 61/901,596 filed Nov. 8, 2013, which claims priority to U.S. Provisional Application Ser. No. 61/952,923 filed Mar. 14, 2014, which claims priority to U.S. Provisional Application Ser. No. 62/055,734 filed Sep. 26, 2014, the contents of each of which are incorporated by reference herein in their entireties.

FIELD OF THE INVENTION

The present invention relates to combination therapies for the treatment of cancer and other diseases and disorders. More specifically, the present invention relates to therapeutic combinations comprising a VEGF antagonist and an anti-CTLA-4 antibody, and methods of use thereof.

BACKGROUND

Vascular endothelial growth factor (VEGF) is a cytokine involved in angiogenesis. The ligand VEGF-A interacts with VEGF receptor-1 (VEGFR1) and VEGFR2, thereby initiating an angiogenesis signaling pathway in normal and tumor vasculature. Antagonists of VEGF are known to be useful for the treatment of a variety of diseases and disorders including cancers, eye diseases and other conditions involving excessive, unwanted or inappropriate angiogenesis. An example of a VEGF antagonist is aflibercept (also known as VEGF Trap; marketed as ZALTRAP®, Regeneron Pharmaceuticals, Inc., Tarrytown, N.Y.). Aflibercept is a VEGF receptor-based chimeric molecule comprising domain 2 from VEGFR1 fused to domain 3 from VEGFR2, which is, in turn, attached through the hinge region to the Fc(a) domain of human IgG1. Aflibercept is approved for the treatment of colorectal cancer and is being developed for the treatment of other cancerous conditions as well. VEGF Trap is described, e.g., in U.S. Pat. No. 7,070,959; see also, Holash et al., *Proc. Natl. Acad. Sci. USA* 99:11393-11398 (2002).

Cytotoxic T-lymphocyte-associated antigen-4 (CTLA-4) is a member of the immunoglobulin superfamily of proteins and is involved in negative regulation of T-cell activation. Upon T cell activation, CTLA-4 is upregulated and competes with CD28 for binding to B7, thereby transmitting a suppressive signal for T cell activation. Antibodies against CTLA-4 have been shown to block the interaction between CTLA-4 and the costimulatory molecules B7.1 and B7.2 (CD80 and CD86). This blockade removes the CTLA-4-mediated inhibitory signal on T-cells and thereby stimulates a natural immune response against cancer cells. Anti-CTLA-4 antibodies have been shown to be clinically effective in the treatment of, e.g., metastatic melanoma. Exemplary anti-CTLA-4 antibodies include ipilimumab (Yervoy®, Bristol-Myers Squibb, disclosed in U.S. Pat. No. 6,984,720) and tremelimumab (Pfizer, disclosed in U.S. Pat. No. 8,491,895).

Although VEGF antagonists and anti-CTLA-4 antibodies have individually shown great promise in the treatment of tumors and other cancerous conditions, more directed, potent and sustained therapeutic options are nonetheless needed for the effective treatment of such diseases and disorders. Accordingly, an unmet need exists in the art for novel therapeutic approaches for the treatment of cancer.

BRIEF SUMMARY OF THE INVENTION

According to one aspect of the present invention, pharmaceutical compositions are provided comprising: (i) a VEGF antagonist; (ii) an anti-CTLA-4 antibody; and (iii) a pharmaceutically acceptable carrier or diluent.

According to another aspect of the present invention, methods are provided for inhibiting or attenuating the growth of a tumor in a subject. The methods according to this aspect of the invention comprise administering to the subject a therapeutically effective amount of a VEGF antagonist and a therapeutically effective amount of an anti-CTLA-4 antibody.

According to another aspect of the present invention, methods are provided for extending or prolonging the survival of a subject afflicted with a tumor. The methods according to this aspect of the invention comprise administering to the subject a therapeutically effective amount of a VEGF antagonist and a therapeutically effective amount of an anti-CTLA-4 antibody.

According to another aspect of the present invention, methods are provided for inducing tumor immunity in a subject. The methods according to this aspect of the invention comprise administering to the subject a therapeutically effective amount of a VEGF antagonist and a therapeutically effective amount of an anti-CTLA-4 antibody. In certain embodiments, the subject treated according to this aspect of the invention is afflicted with a tumor prior to, or at the time of administration of the VEGF antagonist and the anti-CTLA-4 antibody to the subject.

With regard to aspects of the present invention that comprise administering a VEGF antagonist and an anti-CTLA-4 antibody to a subject, the VEGF antagonist and the anti-CTLA-4 antibody can be administered to the subject in separate dosage forms or in a single dosage form (e.g., co-formulation). Various dosing schedules and administration regimens, as disclosed elsewhere herein, are contemplated within these aspects of the invention.

The VEGF antagonist included in and used with the compositions and methods of the present invention may be an anti-VEGF antibody, an anti-VEGF receptor antibody or a VEGF receptor-based chimeric molecule (VEGF Trap). In certain embodiments, the VEGF antagonist is aflibercept.

The anti-CTLA-4 antibody included in and used with the compositions and methods of the present invention may be an antagonist antibody. In certain embodiments, the anti-CTLA-4 antibody is ipilimumab or tremelimumab.

Other embodiments of the present invention will become apparent from a review of the ensuing detailed description.

BRIEF DESCRIPTION OF THE FIGURES

FIG. 1 depicts tumor volume (in $mm^3$) for the different experimental groups at various time points after implantation. FIG. 2 shows the tumor volume (in $mm^3$) of individual mice in each experimental group at Day 22 after implantation. FIG. 3 depicts the percent survival of mice in the different experimental groups at various time points after implantation. Upward arrows along the X-axis indicate the timing of treatment injections. "IgG" is IgG2 isotype control; "Fc" is human Fc control; "hVGT" is aflibercept (aka VEGF Trap); "Anti-CTLA-4" is anti-mouse CTLA-4 IgG2b clone 9D9.

FIG. 4A shows the tumor volume (in $mm^3$) of individual mice in the indicated experimental groups (or naïve [untreated] controls) at Day 14 after the tumor re-challenge; and FIG. 4B shows the tumor volume (in $mm^3$) of individual mice in the indicated experimental groups (or naïve [untreated] controls) at Day 32 after the tumor re-challenge. "IgG" is IgG2 isotype control; "Fc" is human Fc control; "hVGT" is aflibercept (aka VEGF Trap); "Anti-CTLA-4" is anti-mouse CTLA-4 IgG2b clone 9D9.

FIG. 5 depicts tumor volume (in $mm^3$) for the different experimental groups at various time points after implantation. FIG. 6 shows the tumor volume (in $mm^3$) of individual mice in the indicated experimental groups at Day 70 after implantation. FIG. 7 depicts the percent survival of mice in the different experimental groups at various time points after implantation. Upward arrows along the X-axis indicate the timing of treatment injections. "IgG" is IgG2 isotype control; "Fc" is human Fc control; "hVGT" is aflibercept (aka VEGF Trap); "Anti-CTLA-4" is anti-mouse CTLA-4 IgG2b clone 9D9.

FIG. 8 depicts tumor volume (in $mm^3$) for the different experimental groups at various time points after implantation. Upward arrows along the X-axis indicate the timing of treatment injections. FIG. 9 shows the tumor volume (in $mm^3$) of individual mice in each experimental group at Day 21 after implantation.

FIG. 10 shows the extent of tumor regression (scored on a grading scale from 1 to 4) for mice in each treatment group at Day 21. Tumor regression was graded as an estimate of the fraction of the tumor mass that was affected by necrosis, tumoral/peritumoral infiltrates or fibrosis in the H&E sections. Grade 1=0-25%, Grade 2=25-50%, Grade 3=50-75%, Grade 4=75-100%.

FIG. 11 shows the extent of tumor necrosis (scored on a grading scale from 1 to 4) for tumors collected from mice in each treatment group at day 21 and subjected to histopathological examination. Grading was based on the percent of necrotic tissue in the tumor mass. Grade 1=0-25%, Grade 2=25-50%, Grade 3=50-75%, Grade 4=75-100%.

FIG. 12, panels A-C show the extent of inflammatory cell infiltrates, tumor fibrosis, and mitotic figures, respectively, for mice in each treatment group at Day 21. Panel A shows the extent of inflammatory cell infiltrate (scored on a grading scale from 1 to 3). Grade 1=few small aggregates/foci of cells, Grade 2=larger foci of inflammatory cells, Grade 3=confluent foci often becoming locally extensive infiltrates of lymphohistocytic cells bordering and within the tumor mass. Panel B shows the extent of tumor fibrosis (scored on a grading scale from 0 to 2). Fibrosis score was based on Masson's trichrome stain: Grade 0=Rare to occasional collagen fibers scattered throughout the tumor either as part of the tumor stroma or pre-existing collagen around vessels or associated with other structures (e.g. skeletal muscle); or in regions of necrosis where occasional thin collagen strands were considered part of pre-existing tumor stroma; Grade 1=focal to focally extensive deposition of thin collagenous fibers, limited to the tumor borders often overlapping with areas of tumoral/peritiumoral infiltrates or near areas of necrosis; Grade 2=multifocal or locally extensive regions of collagen fiber deposition as described for Grade 1. The fibrous tissue deposited concentrically around the tumor or the pre-existing collagen fibers in the dermis were not included in the estimation. Panel C shows the mitotic figures for the individual treatment groups. Mitotic figures are expressed as the sum of mitotic figures observed in 5 viable non-overlapping high power 40× fields (hpf) per tumor.

FIG. 13 depicts tumor volume (in $mm^3$) for the different experimental groups at various time points after implantation. Upward arrows along the X-axis indicate the timing of treatment injections. FIG. 14 depicts the percent survival of mice in the different experimental groups at various time points after implantation.

FIG. 15 depicts tumor volume (in $mm^3$) for the different experimental groups at various time points after implantation. Upward arrows along the X-axis indicate the timing of treatment injections. FIG. 16 shows the tumor volume (in $mm^3$) of individual mice in the indicated experimental groups at Day 21 after implantation. FIG. 17 depicts the percent survival of mice in the different experimental groups at various time points after implantation.

FIG. 18 depicts tumor volume (in $mm^3$) for the different experimental groups at various time points after implantation. FIG. 19 shows the tumor volume (in $mm^3$) of individual mice in the indicated experimental groups at Day 24 after implantation. "IgG2a" is IgG2a isotype control; "Fc" is human Fc control; "hVGT" is aflibercept (aka VEGF Trap); "Anti-CTLA-4 IgG2a" is an anti-mouse CTLA-4 antibody having an IgG2a isotype.

FIG. 20 depicts tumor volume (in $mm^3$) for the different experimental groups at various time points after implantation. FIG. 21 shows the tumor volume (in $mm^3$) of individual mice in the indicated experimental groups at Day 18 after implantation.

DETAILED DESCRIPTION

Figure 1:
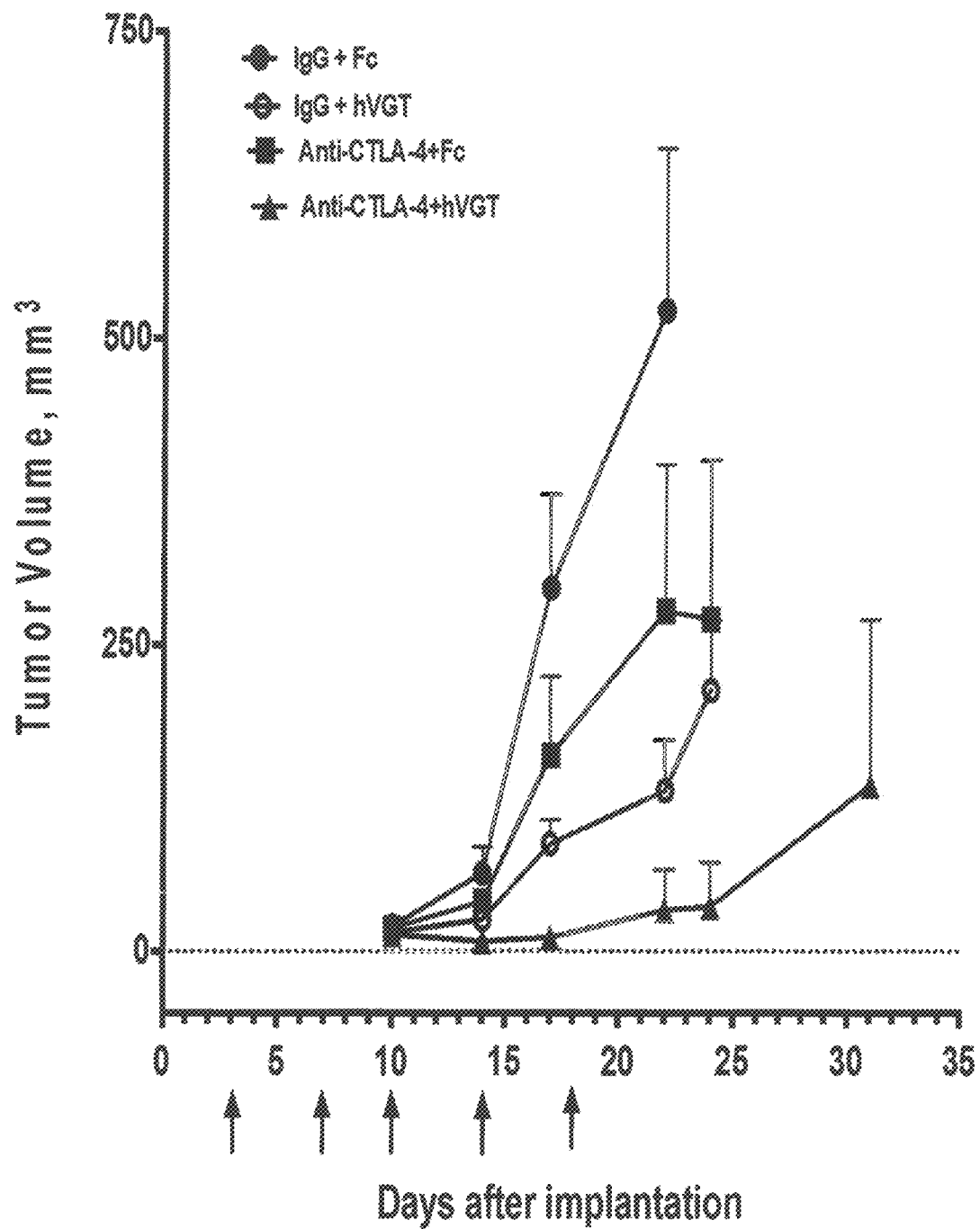
FIGS. 1-3 illustrate tumor growth and survival results for mice implanted with Colon-26 tumor cells at Day 0 and treated with the indicated combinations of molecules by injection at Days 3, 7, 10, 14 and 18 ("early-treatment tumor model").

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

VEGF Antagonists

As used herein, the expression "VEGF antagonist" means any molecule that blocks, reduces or interferes with the normal biological activity of vascular endothelial growth factor (VEGF) or a VEGF receptor. VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies (e.g., bevacizumab [AVASTIN®]), anti-VEGF receptor antibodies (e.g., anti-VEGFR1 antibodies, anti-VEGFR2 antibodies, etc.), and VEGF receptor-based chimeric molecules (also referred to herein as "VEGF-Traps").

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) (also known as aflibercept) which is encoded by the nucleic acid sequence of SEQ ID NO:1. VEGFR1R2-FcΔC1(a) comprises three components: (1) a VEGFR1 component comprising amino acids 27 to 129 of SEQ ID NO:2; (2) a VEGFR2 component comprising amino acids 130 to 231 of SEQ ID NO:2; and (3) a multimerization component ("FcΔC1(a)") comprising amino acids 232 to 457 of SEQ ID NO:2 (the C-terminal amino acid of SEQ ID NO:11 [i.e., K458] may or may not be included in the VEGF antagonist used in the methods of the invention; see e.g., U.S. Pat. No. 7,396,664). Amino acids 1-26 of SEQ ID NO:2 are the signal sequence.

Anti-CTLA-4 Antibodies

As used herein, the expression "anti-CTLA-4 antibody" means any antibody or antigen-binding fragment thereof that specifically binds cytotoxic T lymphocyte-associated antigen-4 (CTLA-4). Human CTLA-4 has the amino acid sequence of SEQ ID NO:3.

Non-limiting, exemplary anti-CTLA-4 antibodies that can be used or included within the methods and compositions of the present invention include, e.g., ipilimumab (Yervoy®, Bristol-Myers Squibb, Princeton, N.J.) and tremelimumab (Pfizer, New York, N.Y.). Other anti-CTLA-4 antibodies that can be used in the context of the present invention include any of the anti-CTLA-4 antibodies as set forth in, e.g., U.S. Pat. Nos. 6,682,736; 6,984,720; 7,605,238; 8,491,895; 8,318,916; 8,263,073; 8,143,379; and references cited therein.

Antibodies

The term "antibody," as used herein (e.g., anti-VEGF antibody, anti-VEGF receptor antibody, anti-CTLA-4 antibody, etc.), includes immunoglobulin molecules comprising four polypeptide chains: two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for VEGF, VEGFR, CTLA-4, or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the compositions and methods of the present invention specifically bind a target antigen (e.g., VEGF, VEGF receptor, CTLA-4, etc.). The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" CTLA-4, as used in the context of the present invention, includes antibodies that bind CTLA-4 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

The antibodies used in the context of the compositions and methods of the present invention may have pH-dependent binding characteristics. For example, an antibody for use in the compositions and methods of the present invention may exhibit reduced binding to its antigen at acidic pH as compared to neutral pH. Alternatively, an antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to an antigen at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CTLA-4 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

The antibodies used in the context of the compositions and methods of the present invention may comprise an Fc domain comprising one or more mutations which enhance or diminish antibody binding to the FcRn receptor, e.g., at acidic pH as compared to neutral pH. For example, the present invention includes antibodies (e.g., anti-VEGF, anti-VEGF receptor, anti-CTLA-4, etc.) comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes methods and compositions comprising antibodies (e.g., anti-VEGF, anti-VEGF receptor, anti-CTLA-4, etc.) comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

The present inventors have demonstrated that the combination of a VEGF antagonist (e.g., VEGF Trap) and an anti-CTLA-4 IgG2a antibody provides superior anti-tumor effects in a mouse model system as compared to the combination of a VEGF antagonist (e.g., VEGF Trap) and an anti-CTLA-4 IgG2b antibody (see, e.g., Example 4, herein below). The human antibody equivalent of mouse IgG2a, which provides ADCC and CDC effector activity, is IgG1. Thus, the present invention includes compositions and methods comprising a VEGF antagonist and an anti-CTLA-4 antibody, wherein the anti-CTLA-4 antibody has an Fc isotype that provides ADCC and CDC effector activity such as IgG1.

Pharmaceutical Compositions Comprising a VEGF Antagonist and an Anti-CTLA-4 Antibody The present invention includes pharmaceutical compositions comprising a VEGF antagonist and an anti-CTLA-4 antibody. The pharmaceutical compositions according to this aspect of the invention may further comprise a pharmaceutically acceptable carrier or diluent. Methods for co-formulating biological therapeutic agents are known in the art and may be used by a person of ordinary skill in the art to make the pharmaceutical compositions of the present invention.

As used herein, the expression "pharmaceutically acceptable carrier or diluent" includes suitable carriers, excipients, and other agents that provide suitable transfer, delivery, tolerance, and the like. Exemplary formulations useful in the context of the present invention can be found in Remington's Pharmaceutical Sciences, Mack Publishing Company, Easton, Pa. Acceptable formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Methods of Treatment and Methods of Administration

The present invention includes methods for inhibiting or attenuating the growth or a tumor in a subject. The methods according to this aspect of the invention comprise administering to the subject a therapeutically effective amount of a VEGF antagonist and a therapeutically effective amount of an anti-CTLA-4 antibody. Inhibition and/or attenuation of tumor growth can be assessed by measuring the size of a tumor in a subject before and after administration of a therapeutic combination of the present invention (e.g., administration of a VEGF antagonist and an anti-CTLA-4 antibody). A reduction in the size of the tumor, or a reduction in the rate of growth of the tumor, following administration of a therapeutic combination of the present invention as compared to the size and/or growth rate of the tumor prior to administration of the therapeutic combination of the present invention indicates an inhibition or attenuation of the growth of a tumor in the subject. In certain embodiments, the methods of the present invention result in tumor regression. According to certain embodiments of the present invention, attenuation of tumor growth means that the rate of tumor growth following administration of a therapeutic combination of the present invention is at least about 5%, 10%, 15%, 20%, 25%, 30%, 35%, 40%, 45%, 50%, 55%, 60%, 65%, 70%, 75%, 80%, 85%, 90%, 95%, or 100% less than the rate of growth the tumor prior to administration of a therapeutic combination of the present invention. As used herein, "attenuation of tumor growth" also includes a reduction in tumor volume (e.g., tumor regression).

The present invention also includes methods for extending or prolonging the survival or a subject afflicted with a tumor. The methods according to this aspect of the invention comprise administering to the subject a therapeutically effective amount of a VEGF antagonist and a therapeutically effective amount of an anti-CTLA-4 antibody. An extension or prolongation of the survival of a subject with a tumor means that the subject, after administration of a therapeutic combination of the present invention (e.g., administration of a VEGF antagonist and an anti-CTLA-4 antibody), has a longer survival time as compared to similarly situated tumor-bearing subjects who receive either no treatment or generally accepted standard of care for the tumor in question. Improved survival time means about 1 week, 2 week, 4 week, 2 month, 4 month, 6 month, 8 month, 10 month, 12 month, 14 month, 16 month, 18 month, 20 month, 22 month, 24 month, 26 month, 28 month, 30 month, 36 month, 40 month, or longer survival as compared to similarly situated tumor-bearing subjects who receive either no treatment or generally accepted standard of care for the tumor in question.

The present invention also includes methods for inducing tumor immunity in a subject. The methods according to this aspect of the invention comprise administering to the subject a therapeutically effective amount of a VEGF antagonist and a therapeutically effective amount of an anti-CTLA-4 antibody. According to certain embodiments of this aspect of the invention, the subject may be afflicted with a tumor prior to being treated with a VEGF antagonist and an anti-CTLA-4 antibody, and following such treatment becomes immune or resistant to future tumors. As used herein, induction of tumor immunity means that a subject is resistant to, or substantially resistant to future tumors after receiving a therapeutic combination of the present invention. Tumor immunity also means that a subject who formerly was afflicted with a tumor and is successfully treated (e.g., by administration of a therapeutic combination of the present invention), will not experience the development of the same or similar tumor type in the future.

According to certain embodiments, the methods of the present invention may comprise administering the VEGF antagonist and the anti-CTLA-4 antibody to the subject in separate dosage forms. For example, the VEGF antagonist and the anti-CTLA-4 antibody may be delivered to the subject in separate injections, infusions, or other means of drug delivery known in the art. When administered separately, the separate dosage forms (i.e., one comprising a VEGF antagonist and the other comprising an anti-CTLA-4 antibody) may be administered to the subject simultaneously or sequentially. If administered simultaneously, both agents are administered to the subject within the time span of less than about 1 minute. If administered sequentially, one agent is administered at a first time point and the other agent is administered at a second, later time point. The second time point may be 1 minute, 2 minutes, 5 minutes, 10 minutes, 20 minutes, 30 minutes, 1 hour, or longer after than the first time point. In certain embodiments, the VEGF antagonist is administered first, followed by administration of the anti-CTLA-4 antibody. In other embodiments, the anti-CTLA-4 antibody is administered first, followed by administration of the VEGF antagonist.

According to the methods of the present invention, the VEGF antagonist and the anti-CTLA-4 antibody may be administered to the subject in separate dosage forms at the same frequency of administration (e.g., once a week, once every two weeks, once every four weeks, once every eight weeks, once every ten weeks, once every twelve weeks, etc.). Alternatively, the two agents may be administered to the subject in separate dosage forms at different frequencies of administration. For example, the VEGF antagonist may be administered to the subject more frequently than the anti-CTLA-4 antibody; or the anti-CTLA-4 antibody may be administered to the subject more frequently than the VEGF antagonist.

According to certain embodiments, the methods of the present invention may comprise administering the VEGF antagonist and the anti-CTLA-4 antibody to the subject in a single dosage form. As used herein, a "single dosage form"

means a composition comprising both a VEGF antagonist and an anti-CTLA-4 antibody. The single dosage form may, in certain embodiments, comprise one or more pharmaceutically acceptable carriers or diluents as disclosed elsewhere herein. Methods for co-formulating two or more biological therapeutics into a single dosage form are known in the art and may be used, as appropriate, in the context of this aspect of the invention.

The methods and compositions of the present invention are useful for the treatment of primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. Specific cancers that are treatable according to the methods and compositions of the present invention include, e.g., renal cell carcinoma, pancreatic carcinoma, breast cancer, prostate cancer, hepatocellular carcinoma, colorectal cancer, malignant mesothelioma, multiple myeloma, ovarian cancer, glioblastoma, and melanoma.

In certain embodiments, the methods and compositions of the present invention are useful for the treatment of anti-VEGF-resistant tumors in a subject. An "anti-VEGF-resistant tumor," as used herein, means a tumor that does not respond, or only partially responds, to treatment with an anti-VEGF agent such as an anti-VEGF antibody, an anti-VEGF receptor antibody, or any other VEGF-specific binding protein (including, e.g., a VEGF-trap, as defined herein). For example, an anti-VEGF-resistant tumor can be, e.g., a tumor that, when contacted with an amount of VEGF antagonist that is ordinarily capable of inhibiting or attenuating the growth of at least one type of tumor, continues to grow and/or proliferate in vitro or in vivo (e.g., in cell culture or when implanted into an animal). An anti-VEGF-resistant tumor may be a tumor derived from tumor cells that originally responded to anti-VEGF therapy, but through selection, mutation or adaptation, have acquired resistance to one or more anti-VEGF agents.

The subjects that are treatable using the methods and compositions of the present invention include any subject diagnosed with cancer or identified as having a tumor. In certain embodiments, the subject is a patient who has been diagnosed or identified as having a tumor that is at least partially resistant to anti-VEGF treatment. Methods for diagnosing a patient as having an anti-VEGF resistant tumor will be known to persons of ordinary skill in the art and can be practiced using routine diagnostic methods.

Additional Therapeutic Agents

The present invention includes compositions and therapeutic formulations comprising a VEGF antagonist and an anti-CTLA-4 antibody in combination with one or more additional therapeutically active components, and methods of treatment comprising administering such combinations to subjects in need thereof.

Additional therapeutically active components that may be combined with and/or administered in combination with a VEGF antagonist and an anti-CTLA-4 antibody in the context of the present invention include, e.g., one or more of the following: an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody or small molecule kinase inhibitor such as, e.g., imatinib mesylate or sunitinib malate), a PDGF ligand inhibitor (e.g., anti-PDGF-A, -B, -C, or -D antibody, aptamer, siRNA, etc.), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), etc. Other agents that may be beneficially administered or co-formulated in combination with a VEGF antagonist and anti-CTLA-4 antibody include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention includes compositions, therapeutic formulations, and methods of treatment comprising a VEGF antagonist and an anti-CTLA-4 antibody in combination with one or more chemotherapeutic agents. Examples of chemotherapeutic agents useful in the context of this aspect of the invention include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, irinotecan, leucovorin, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and antiandrogens such as flutamide, nilutamide, bicalutamide, leuprolide, and goserelin; and pharmaceutically acceptable salts, acids or derivatives of any of the above.

The present invention also includes compositions, therapeutic formulations, and methods of treatment comprising a VEGF antagonist and an anti-CTLA-4 antibody in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives or combinations thereof, may be administered just prior to, concurrent with, or shortly after the administration of a VEGF antagonist and/or an anti-CTLA-4 antibody, within the context of the present invention; (for purposes of the present disclosure, such administration regimens are considered the administration of a VEGF antagonist and an anti-CTLA-4 antibody "in combination with" an additional therapeutically active component). The present invention includes pharmaceutical compositions in which a VEGF antagonist and/or an anti-CTLA-4 antibody is/are co-formulated with one or more of the additional therapeutically active component(s) as described elsewhere herein.

Drug Delivery and Methods of Administration

Various delivery systems are known and can be used to administer the pharmaceutical compositions of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition(s) may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention (comprising, e.g., a single therapeutically active agent, or a combination of two or more therapeutically active agents) can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of active ingredient(s) (e.g., VEGF antagonist and/or anti-CTLA-4 antibody) contained within the pharmaceutical compositions of the present invention, and/ or administered to a subject according to the methods of the present invention, is generally a therapeutically effective amount. As used herein, the expression "therapeutically effective amount," in the context of a VEGF antagonist and/or an anti-CTLA-4 antibody, means an amount of the therapeutic agent, alone or in combination with another therapeutic agent, that is capable of producing a measurable biological effect in a human or animal subject. Examples of such measurable biological effects include, e.g., detection of the therapeutic molecule in the serum of the subject, detection of relevant metabolic products in a biological sample taken from the subject, a change in the concentration of a relevant biomarker in a sample taken from the subject, a reduction in tumor size, a reduction in tumor growth rate, tumor regression, improved survival of the subject, and/or an improvement in any other relevant therapeutic or clinical parameter.

In the case of a VEGF antagonist (e.g., VEGF Trap) or an anti-CTLA-4 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the VEGF antagonist or anti-CTLA-4 antibody.

The amount of VEGF antagonist (e.g., VEGF Trap) and/or anti-CTLA-4 antibody administered to a subject may be expressed in terms of milligrams of antibody per kilogram of subject body weight (i.e., mg/kg). For example, the VEGF antagonist (e.g., VEGF Trap) and/or anti-CTLA-4 antibody may be administered to a patient at a dose of about 0.0001 to about 10 mg/kg of subject body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Anti-Tumor Effects of a Combination of an Anti-CTLA-4 Antibody and a VEGF Antagonist in a Mouse Early-Treatment Tumor Model An early-treatment tumor model was developed to test the efficacy of a combination of an anti-CTLA-4 antibody and a VEGF antagonist. In this model, the combination therapy was administered shortly after tumor implantation. The anti-CTLA-4 antibody used in this experiment was anti-mouse CTLA-4 IgG2b clone "9D9" (Bio X Cell, West Lebanon, N.H., Cat. No. BE0164). The VEGF antagonist used in this experiment was aflibercept (a VEGF receptor-based chimeric molecule, also known as "VEGF-trap" or "VEGFR1R2-FcΔC1(a)," a full description of which is provided elsewhere herein).

For this experimental model, $1.0 \times 10^6$ Colon-26 tumor cells were implanted into mice at Day 0. Starting on Day 3, prior to the establishment of measurable tumors, mice were treated with one of the mono- or combination therapies, or control combination, as set forth in Table 1:

TABLE 1

| Treatment Group | First Agent | Second Agent |
| --- | --- | --- |
| Control Combination | IgG2b isotype control (100 μg, IP) | hFc control (10 mg/kg SC) |
| VEGF Trap only | IgG2b isotype control (100 μg, IP) | Aflibercept (10 mg/kg, SC) |
| anti-CTLA-4 only | anti-CTLA-4 mAb 9D9 (100 μg, IP) | hFc control (10 mg/kg SC) |
| VEGF Trap + anti-CTLA-4 | anti-CTLA-4 mAb 9D9 (100 μg, IP) | Aflibercept (10 mg/kg, SC) |

The various therapies were administered at five different time points over a two week period (i.e., injections at Day 3, Day 7, Day 10, Day 14 and Day 18).

Animals in each therapy group were evaluated in terms of tumor incidence, tumor volume, median survival time, and number of tumor-free animals at Day 50 (i.e., for 50 days). The extent of tumor growth is summarized in FIG. 1 (tumor growth curves) and FIG. 2 (Tumor volume at Day 22), and percent survival over time is depicted in FIG. 3. Results are also summarized in Table 2.

TABLE 2

| Treatment Group | Median Survival Time | Tumor Incidence @ Day 17 | No. of Tumor-Free Animals by Day 50 |
| --- | --- | --- | --- |
| Control Combination | 24 days | 9/10 | 1/10 |
| VEGF Trap only | 35 days | 8/10 | 0/10 |
| anti-CTLA-4 only | 42 days | 7/10 | 3/10 |
| VEGF Trap + anti-CTLA-4 | >50 days (70%) | 3/10 | 7/10 |

Figure 2:
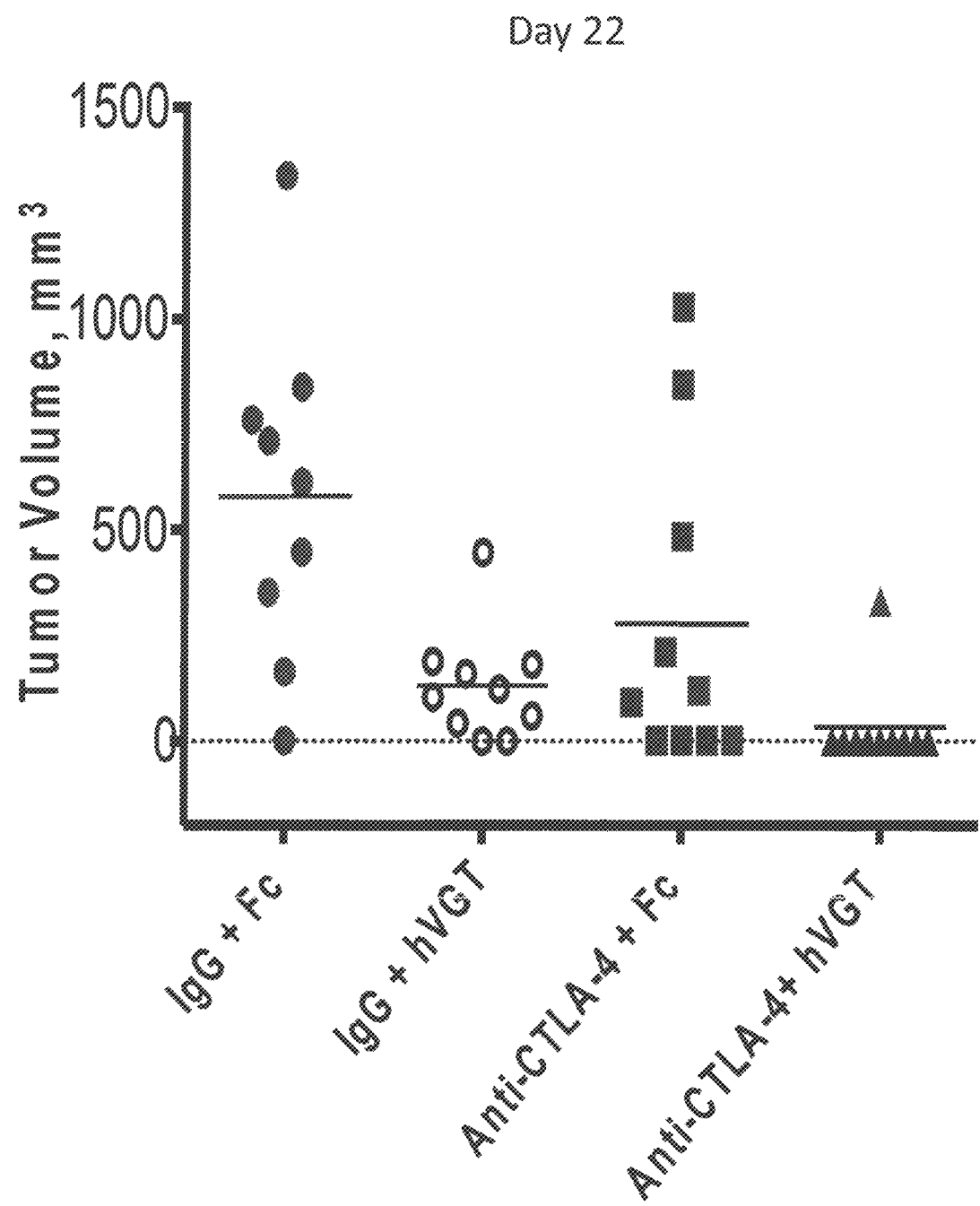
Figure 3:
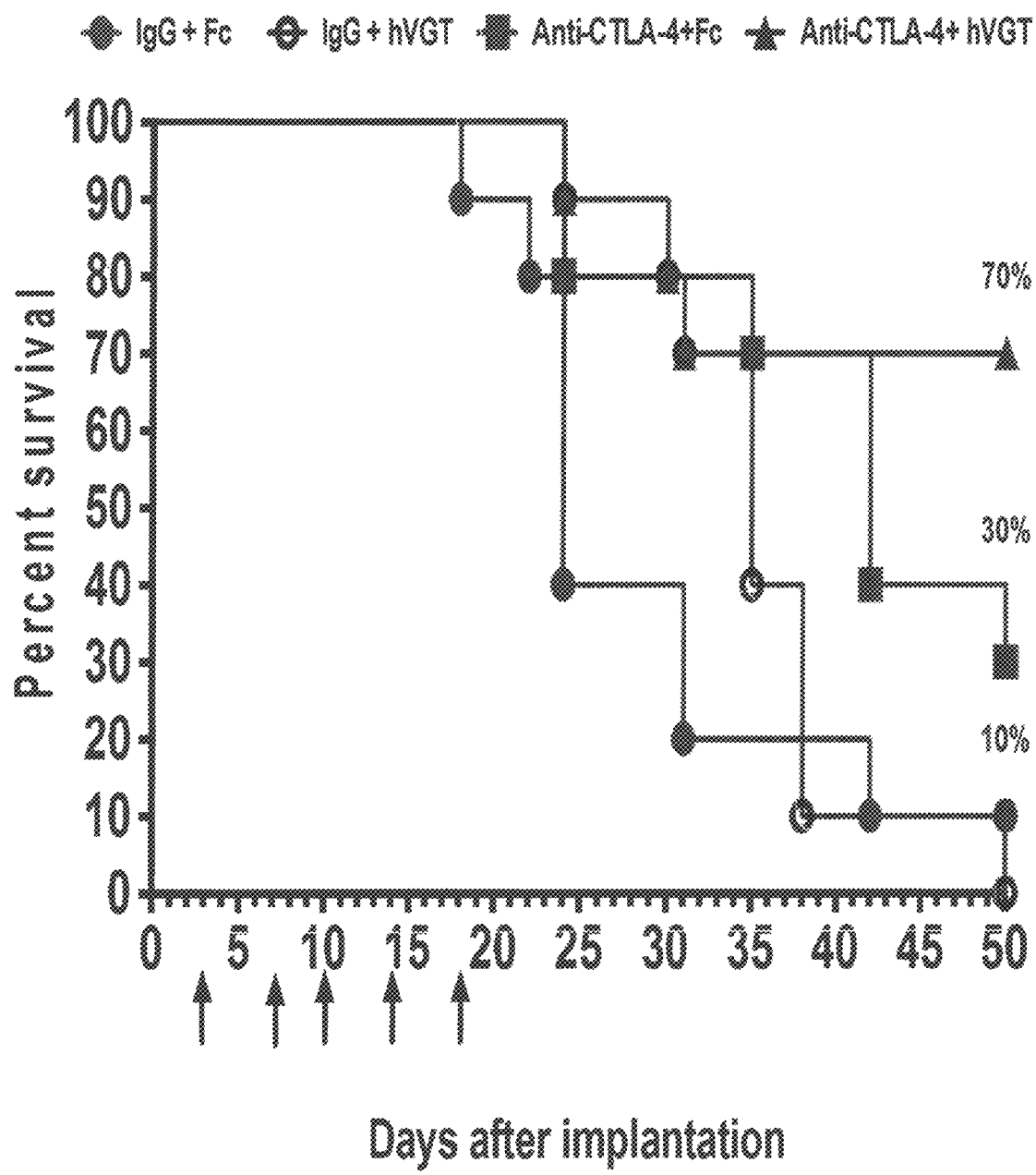

Tumor growth was substantially reduced in animals treated with the combination of VEGF Trap+anti-CTLA-4 antibody as compared to the single agent treatment groups (see FIGS. 1 and 2). Furthermore, survival was substantially increased in the VEGF Trap+anti-CTLA-4 antibody group, with 70% of animals surviving to at least day 50 after tumor implantation. By contrast, for the anti-CTLA-4 and VEGF Trap monotherapy groups, survival to Day 50 was only 30% and 0% respectively (see FIG. 3 and Table 2).

Thus this Example demonstrates that the combination of an anti-CTLA-4 antibody and a VEGF antagonist, when administered at an early point in the tumor development process, can inhibit tumor growth and improve survival to a much greater extent than either therapeutic agent alone.

Example 2

Tumor Immunity of Animals Previously Treated with a Combination of an Anti-CTLA-4 Antibody and a VEGF Antagonist in a Mouse Early-Treatment Tumor Model As a follow-up to Example 1, tumor-free animals from the various treatment groups (See Tables 1 and 2) were selected and re-challenged with $1.0 \times 10^6$ Colon-26 tumor cells at Day 60 following the initial tumor implantation. Also included in this experiment as controls were naïve animals that had not been subjected to tumor challenge or treatment. The various treatment groups for this follow-up experiment are summarized in Table 3.

TABLE 3

| Treatment Group | No. of Tumor-Free Animals Following Initial Challenge |
| --- | --- |
| Control Combination (IgG + hFc) | 1 |
| VEGF Trap only | 0 |
| anti-CTLA-4 only | 3 |
| VEGF Trap + anti-CTLA-4 | 6 |
| Naïve Group A | 10 |
| Naïve Group B | 10 |

Figure 4A:
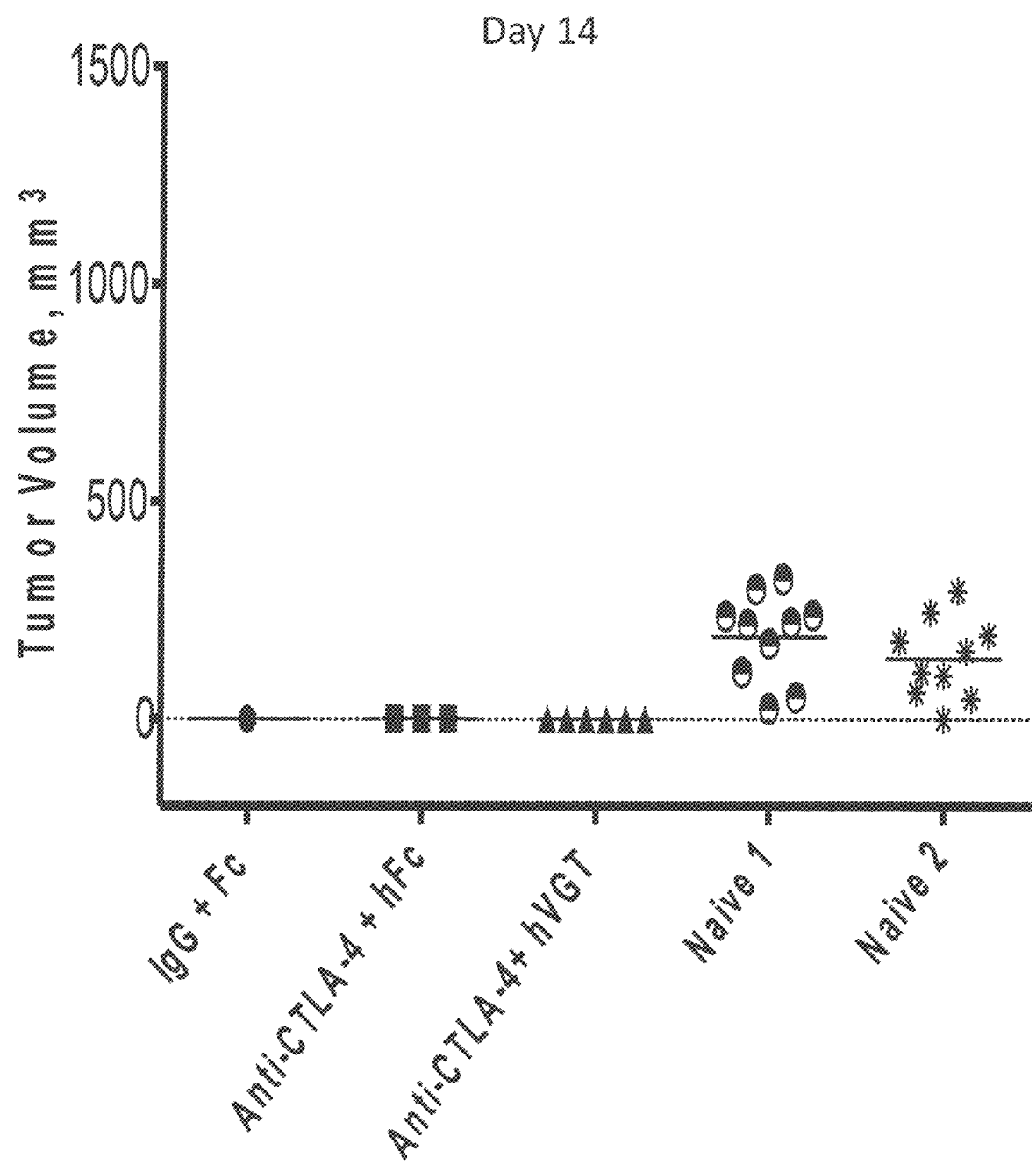
FIGS. 4A-4B illustrate tumor volume measurements in mice that were tumor free after an initial tumor challenge and treatment with the indicated combinations of molecules, and then re-challenged with Colon-26 tumor cells at Day 60 after the initial tumor implantation (without additional treatments).
Figure 4B:
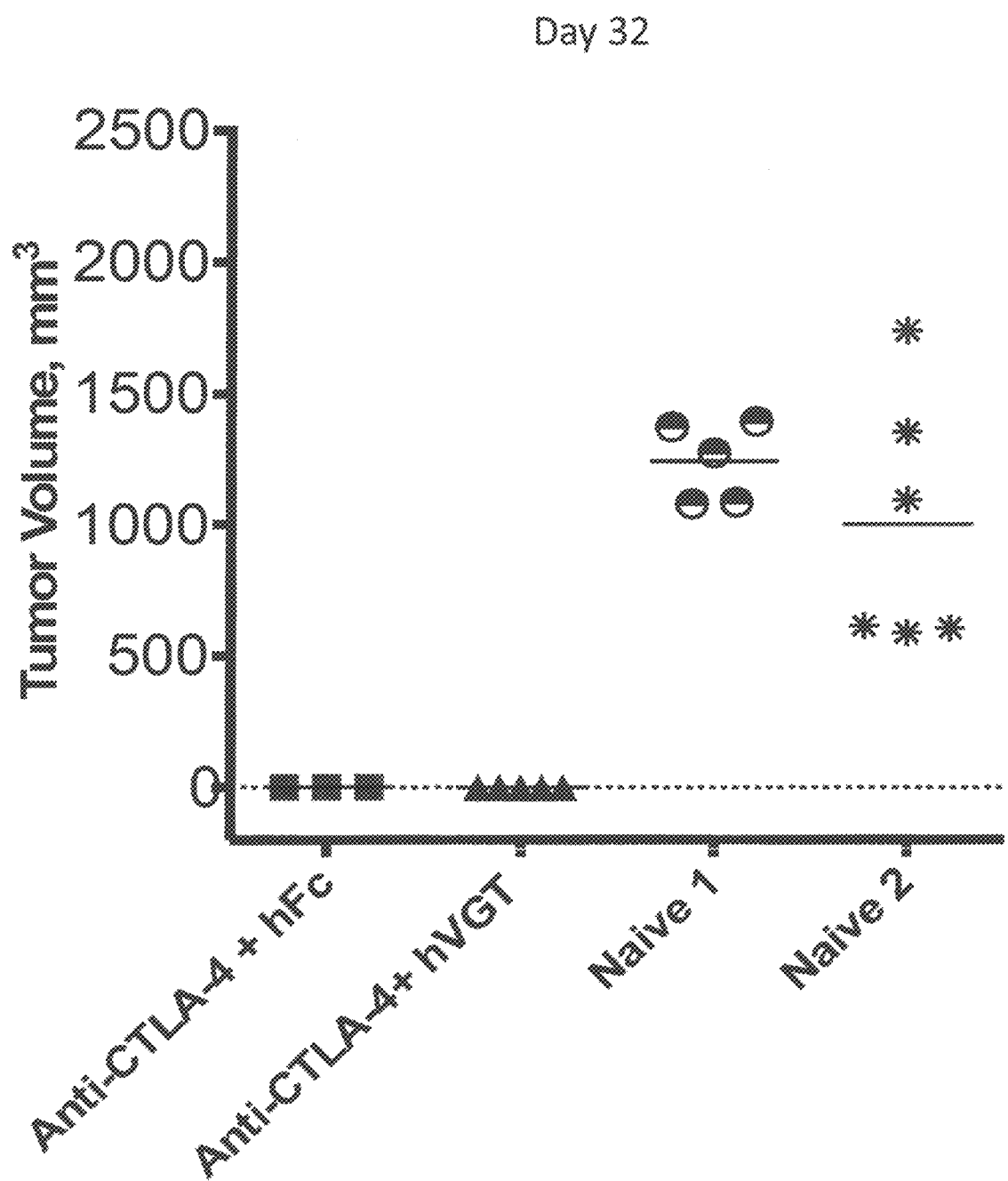

The animals from each treatment group were implanted with $1 \times 10^6$ Colon-26 tumor cells at Day 60 following the initial tumor cell implantation (see Example 1). Tumor volume and survival were assessed 14 and 32 days after the tumor re-challenge. Results are summarized in FIGS. 4A and 4B. As shown, the anti-CTLA-4 only and VEGF Trap+ anti-CTLA-4 animals remained tumor-free throughout the course of the experiment (i.e., through Day 32), whereas naïve animals that had not received any therapeutic pre-treatment developed tumors as expected. All three animals in the anti-CTLA-4 only group survived the re-challenge, and 5 out of 6 animals in the VEGF Trap+anti-CTLA-4 group survived the tumor re-challenge to the end of the experiment (Day 32).

This Example demonstrates that treatment with an anti-CTLA-4 antibody alone or in combination with a VEGF antagonist induces an immunologic memory response that protects treated subjects from future tumor challenges.

Example 3

Anti-Tumor Effects of a Combination of an Anti-CTLA-4 Antibody and a VEGF Antagonist in a Mouse Late-Treatment Tumor Model In Example 1, mice were subjected to therapeutic treatments shortly after tumor implantation. In this Example, by contrast, treatment was intentionally delayed until after tumors were established. The experiment was carried out as follows: On Day 0, $1 \times 10^6$ Colon-26 tumor cells were implanted into mice. On Day 11, after tumors had grown to approximately 60 mm³, mice were randomized into groups with the same average tumor size and treated with one of the mono- or combination therapies, or control combination, as used in Example 1 (see Table 1). The various therapies were administered at five different time points over a two week period (i.e., injections at Day 11, Day 15, Day 17, Day 21 and Day 25).

Figure 5:
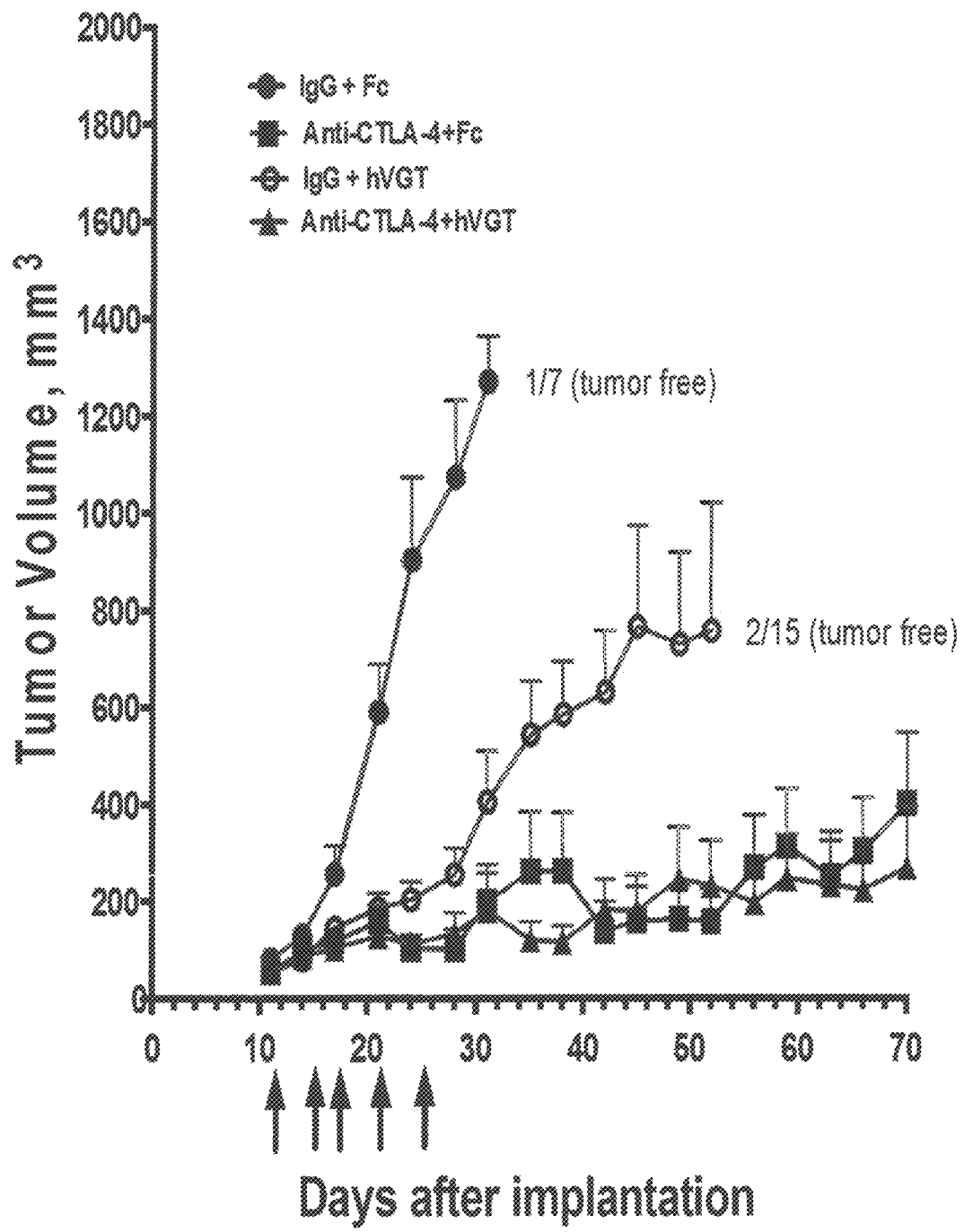
FIGS. 5-7 illustrate tumor growth and survival results for mice implanted with Colon-26 tumor cells at Day 0 and treated with the indicated combinations of molecules by injection at Days 11, 15, 17, 21 and 25 ("late-treatment tumor model").
Figure 6:
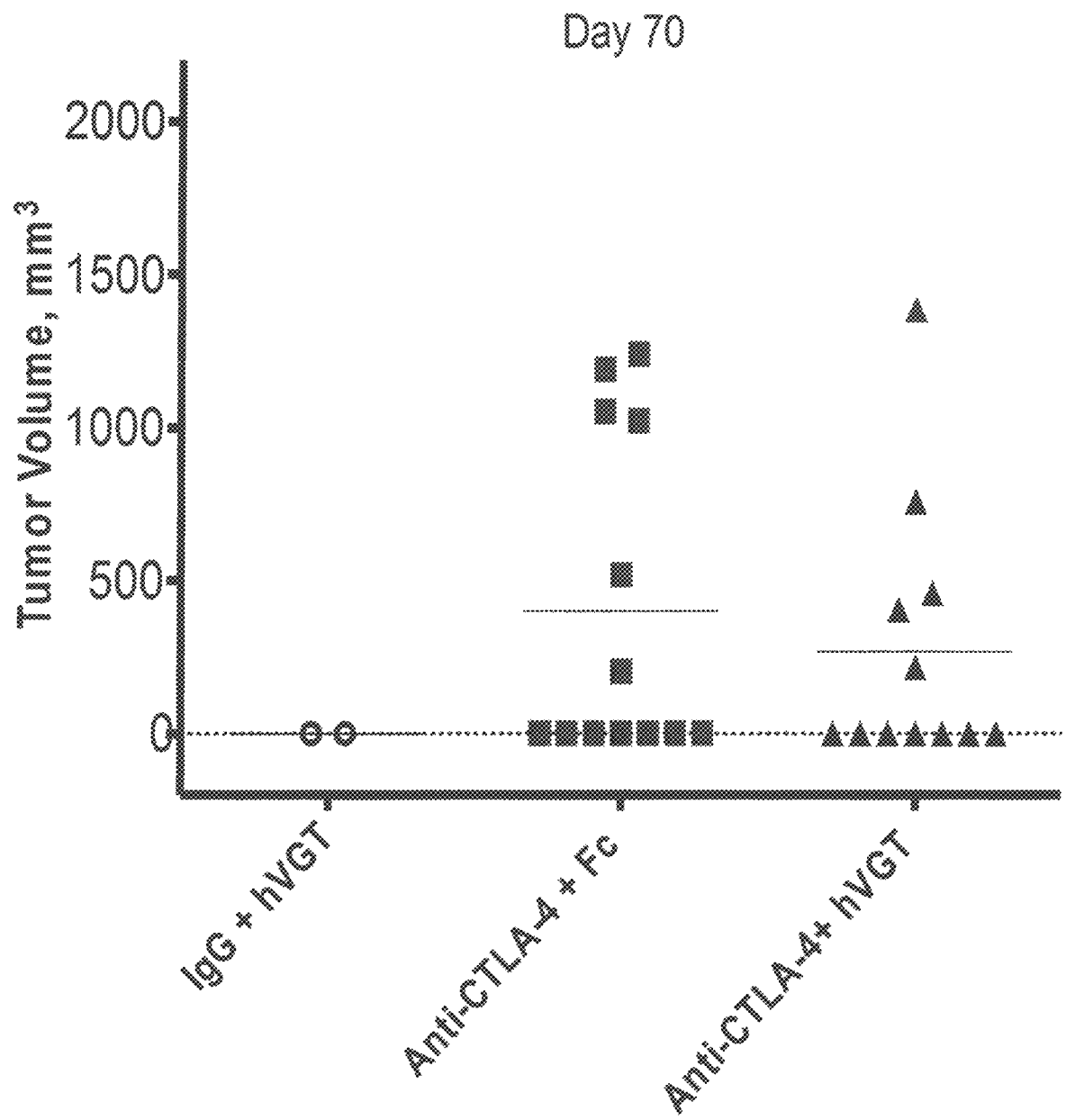
Figure 7:
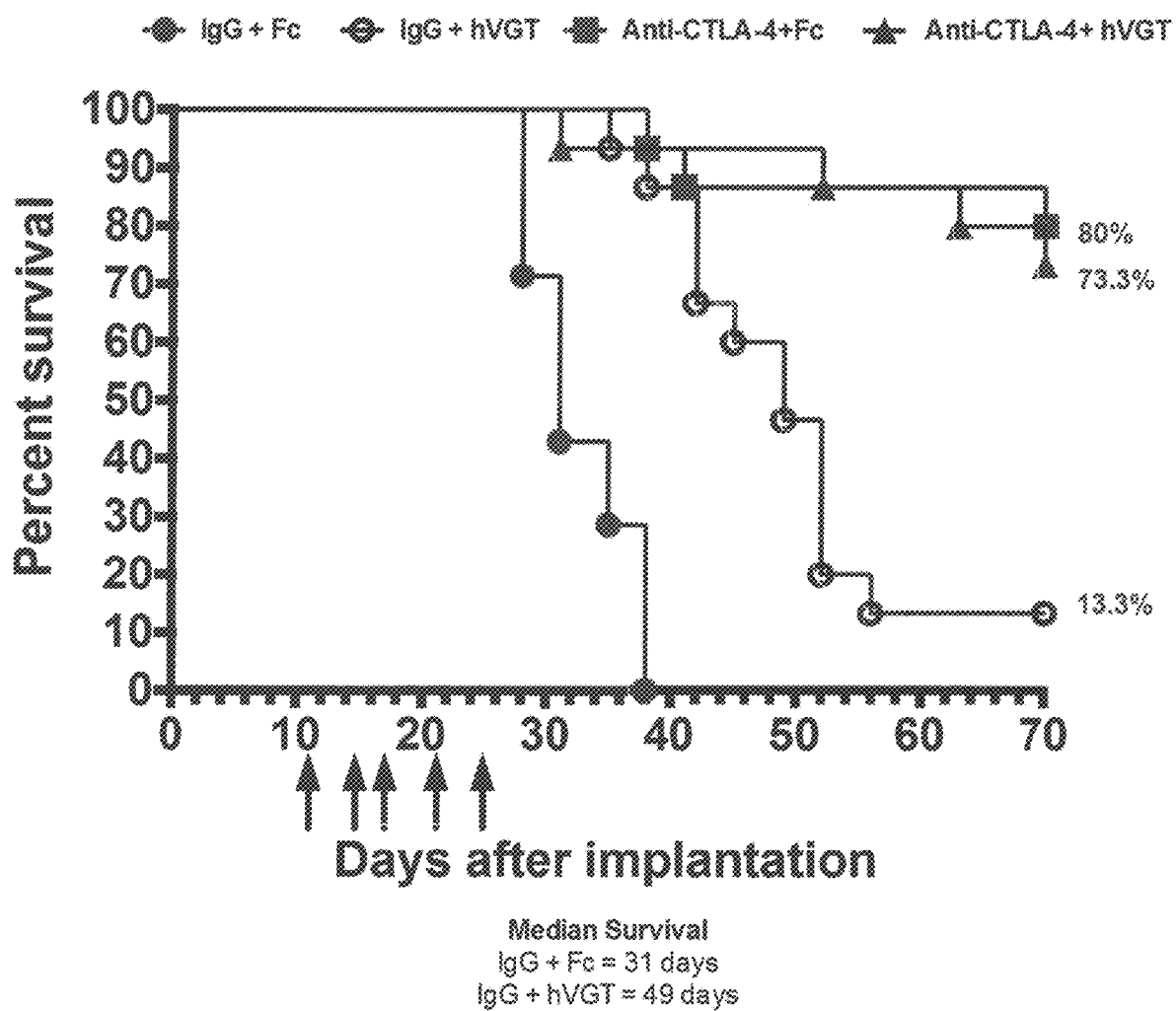

Animals in each therapy group were evaluated in terms of tumor incidence, tumor volume, median survival time, and number of tumor-free animals up to Day 70. The extent of tumor growth is summarized in FIG. 5 (tumor growth curves) and FIG. 6 (Tumor volume at Day 70), and percent survival is depicted in FIG. 7. Results are also summarized in Table 4.

TABLE 4

| Treatment Group | Median Survival Time | No. of Tumor-Free Animals by Day 70 |
| --- | --- | --- |
| Control Combination | 31 days | 0/7 |
| VEGF Trap only | 49 days | 2/15 |
| anti-CTLA-4 only | >70 days | 7/15 |
| VEGF Trap + anti-CTLA-4 | >70 days | 7/15 |

In the late-treatment model, anti-tumor responses were observed in the anti-CTLA-4 mono-treatment group, as well as in the VEGF Trap+anti-CTLA-4 combination treatment group. In addition, enhanced survival was observed in the anti-CTLA-4 mono-treatment group as well as in the VEGF Trap+anti-CTLA-4 combination treatment group, with median survival percentages of 86% and 80%, respectively, by day 70.

Figure 8:
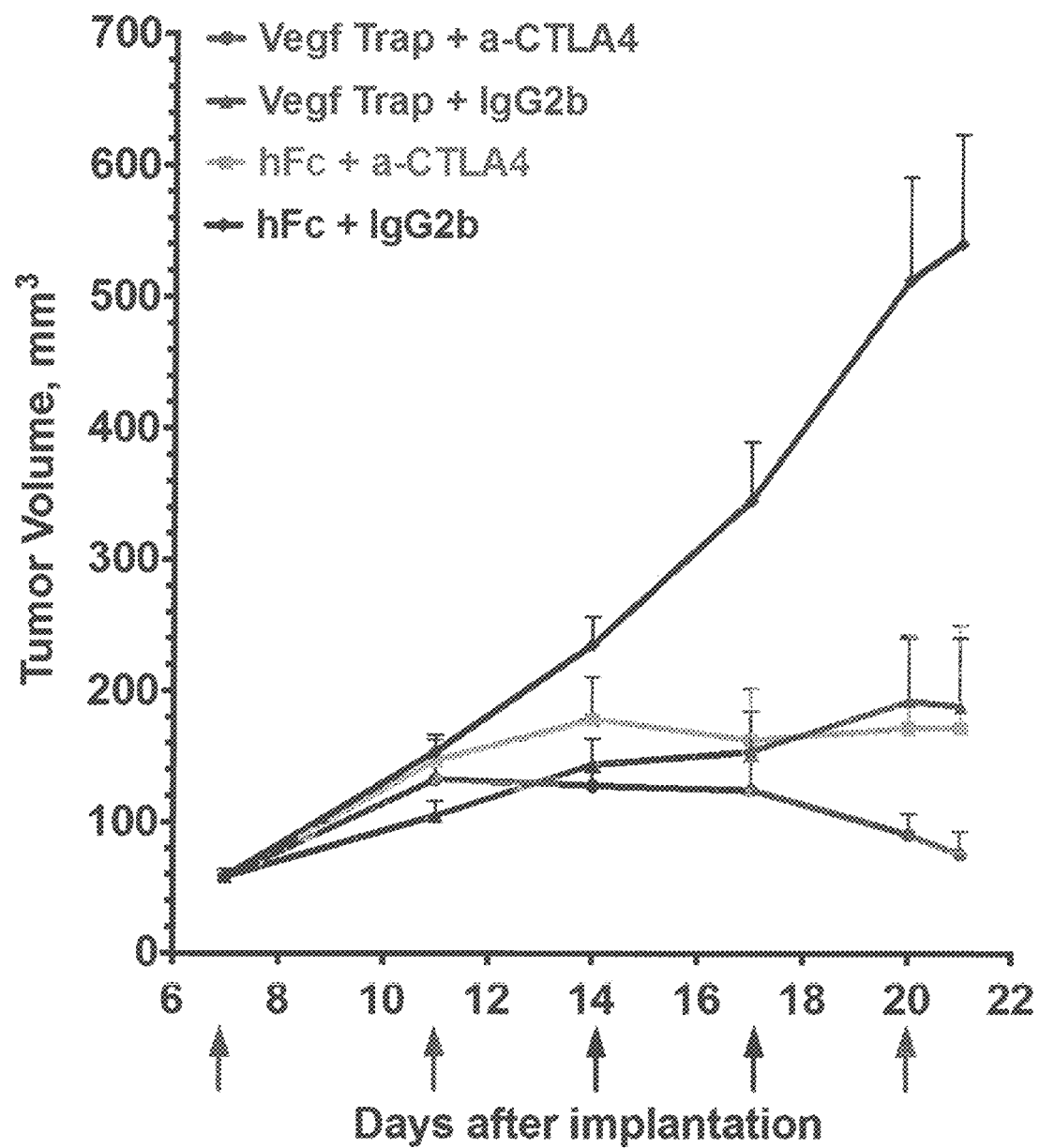
FIGS. 8-12 illustrate tumor growth, regression, necrosis and histopathological parameters in mice treated with the indicated single or combination therapies, or control combinations, starting at seven days after Colon-26 tumor implantation.
Figure 9:
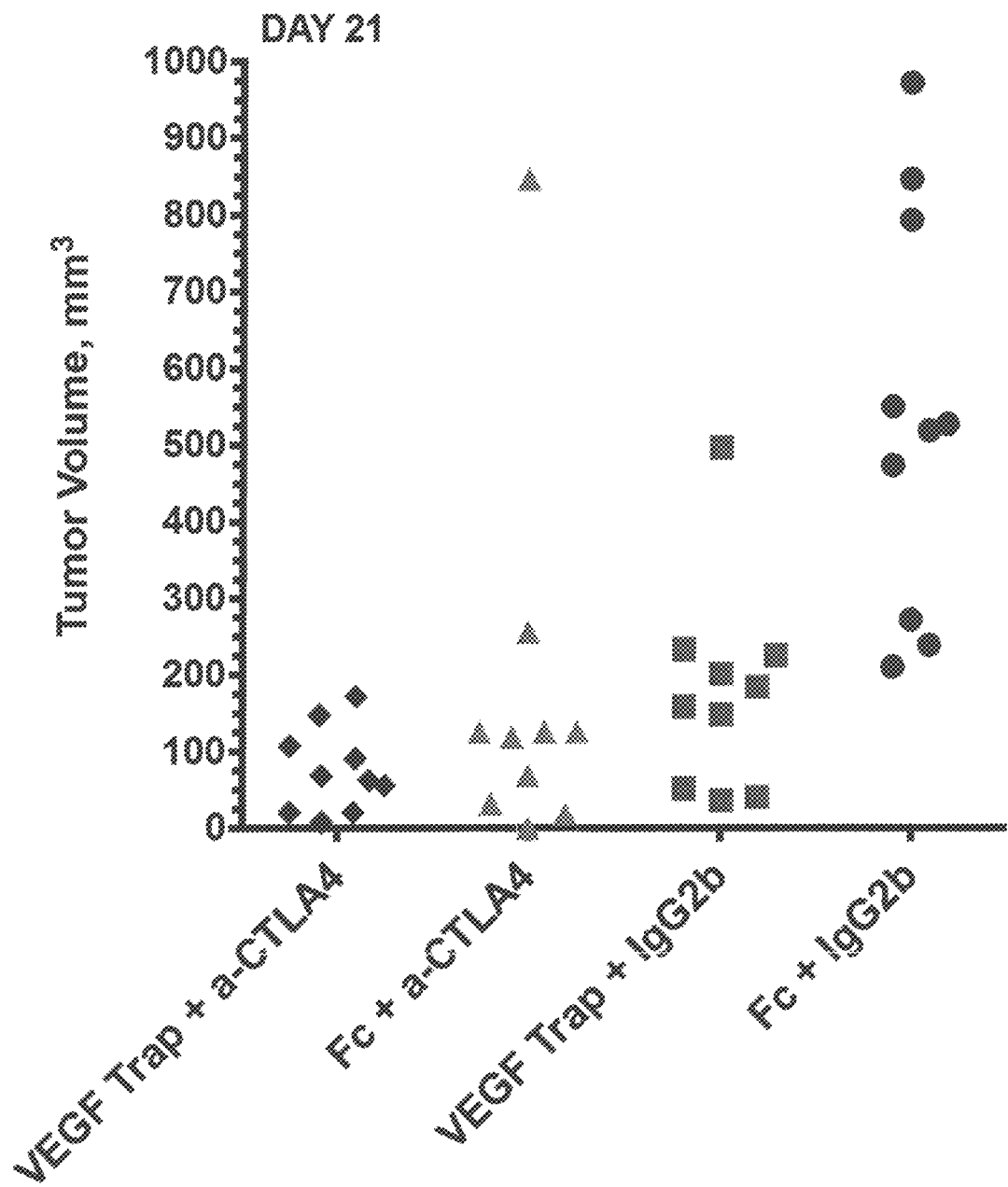
Figure 10:
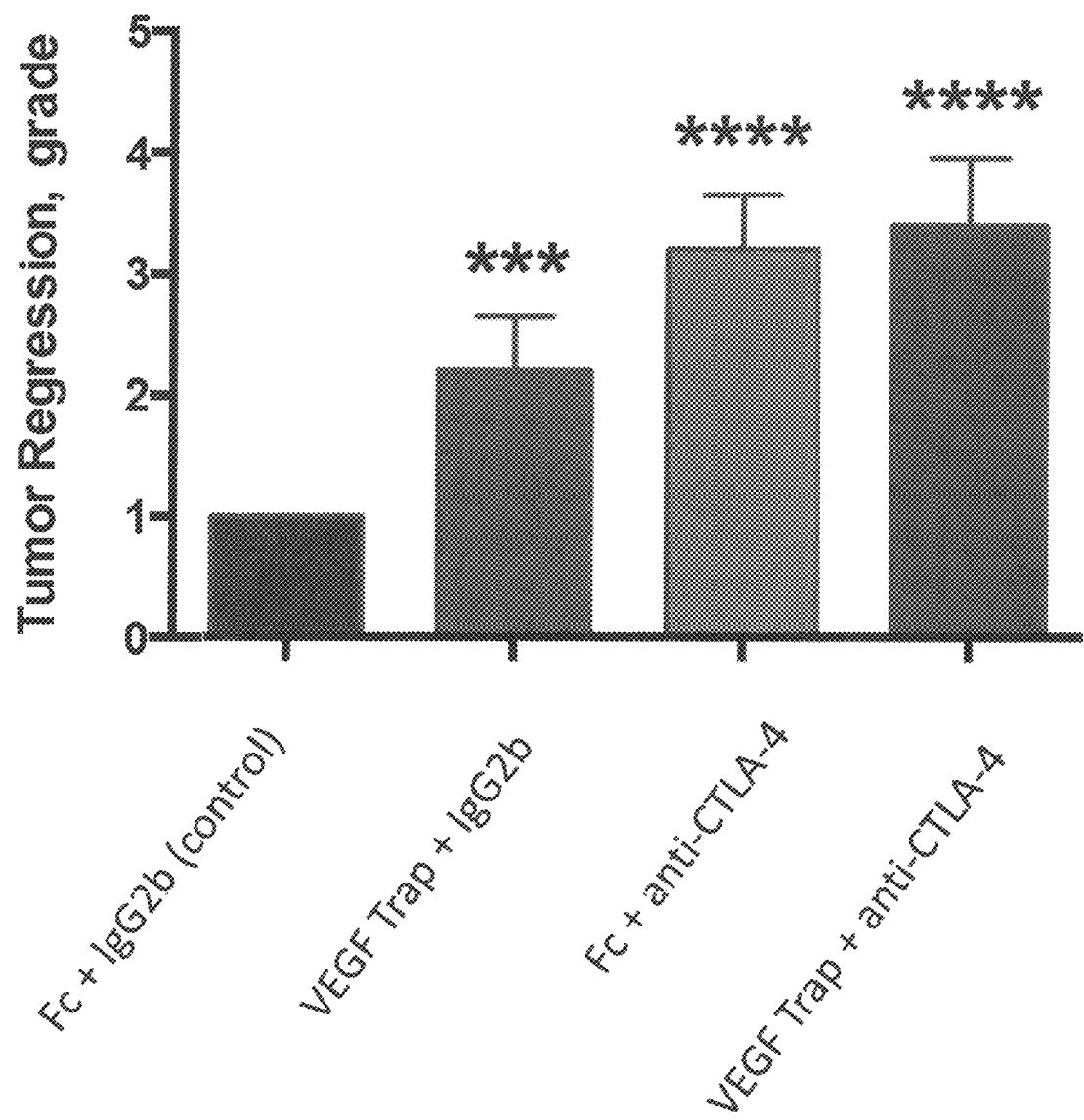
Figure 11:
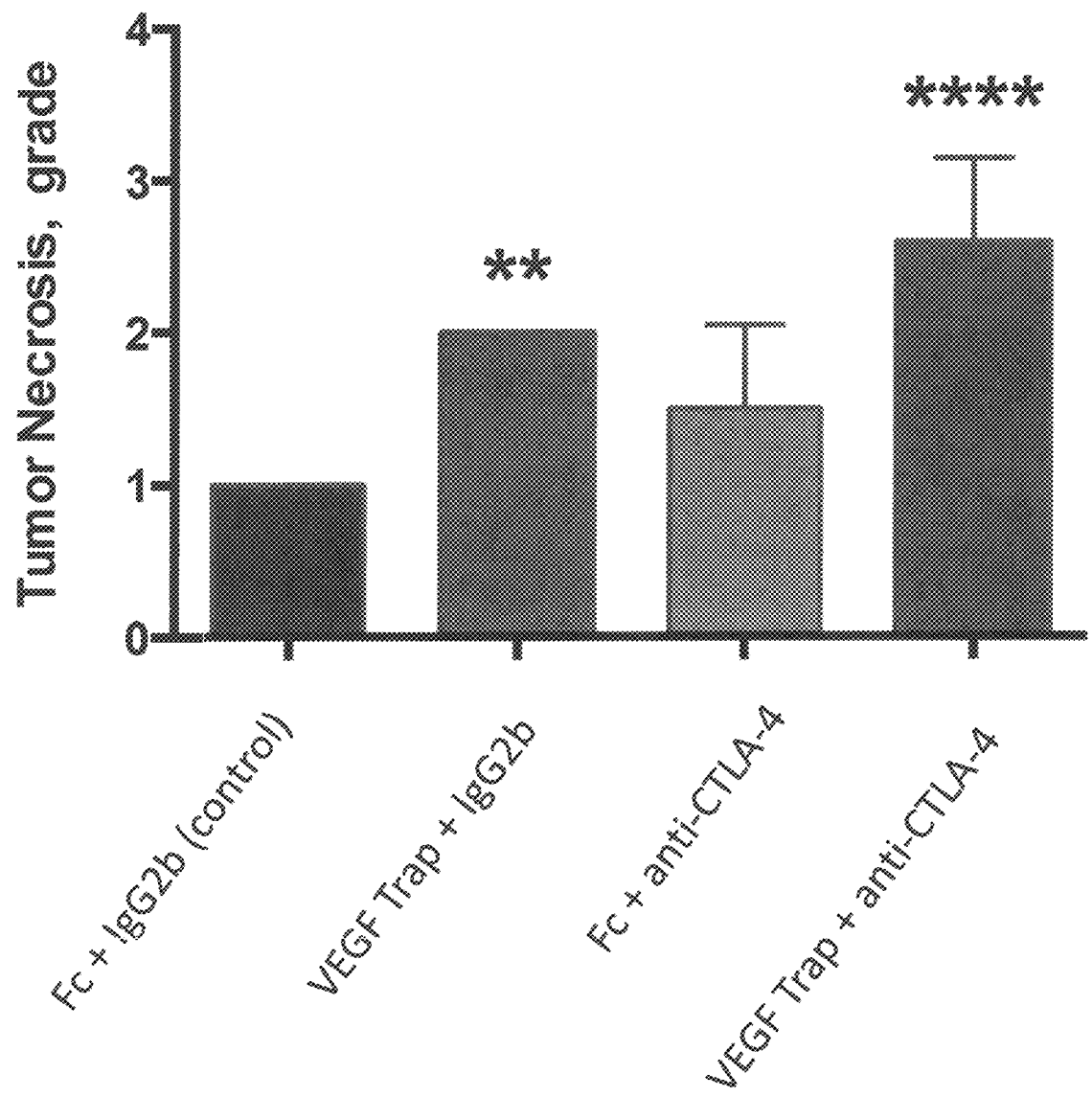

A similar experiment was then carried out to evaluate the effect of the VEGF Trap+anti-CTLA-4 combination, as well as the various single agent and control combinations, on tumor growth and histopathological characteristics of individual tumors in a Colon-26 tumor model. Briefly, 40 Balb/c adult male mice (7-8 weeks old) were implanted with Colon-26 tumor cells on Day 0 ($1 \times 10^6$ Colon-26 tumor cells per mouse injected into the right flank). Tumors were allowed to grow to an approximate volume of 60-80 mm³ (by Day 7). On post-implantation Day 7, mice were divided into groups and treated with one of the mono- or combination therapies, or control combination, as used in Example 1 (see Table 1). The various therapies were administered to the mice at five different time points (i.e., injections at Day 7, Day 11, Day 14, Day 17, and Day 20). Tumor volume was measured over the course of the treatment period. On post-implantation Day 21, 5 tumors were collected from mice in each treatment group for pathological evaluation. Tumors were excised together with adjacent skin flap, and fixed by immersion into a freshly made and pH-balanced 10% formalin solution for 24 hours, then rinsed with 70% ethanol and stored in 70% ethanol at room temperature. Paraffin-embedded tumors were sectioned and stained with H&E and Masson's trichrome histological special stains. Tumor volumes are shown in FIGS. 8 and 9; Tumor regression and necrosis at Day 21 are shown in FIGS. 10 and 11, respectively.

The results of this second experiment confirm that anti-CTLA-4 or VEGF Trap each suppressed the growth rate of established Colon-26 tumors as single agents, and that the combination therapy (VEGF Trap+anti-CTLA-4) caused an even greater reduction in tumor growth in this model. It was also observed in this model that anti-CTLA4 antibody therapy increases the density of tumor-infiltrating CD8+ T cells, but not CD4+ T cells.

Histopathological evaluation of tumors in this experiment revealed tumor regression promoted by both anti-CTLA-4 and VEGF Trap therapies; however, the mechanism by which each agent promoted tumor regression appeared to be different. In particular, VEGF Trap treatment promoted increased tumor necrosis, whereas anti-CTLA-4 treatment alone did not promote a definitive increase in tumor necrosis (FIG. 11). The combination of VEGF Trap+anti-CTLA-4 treatment resulted in increased tumor necrosis that was significantly greater than what was observed in the VEGF Trap treatment group alone (FIG. 11).

Figure 12:
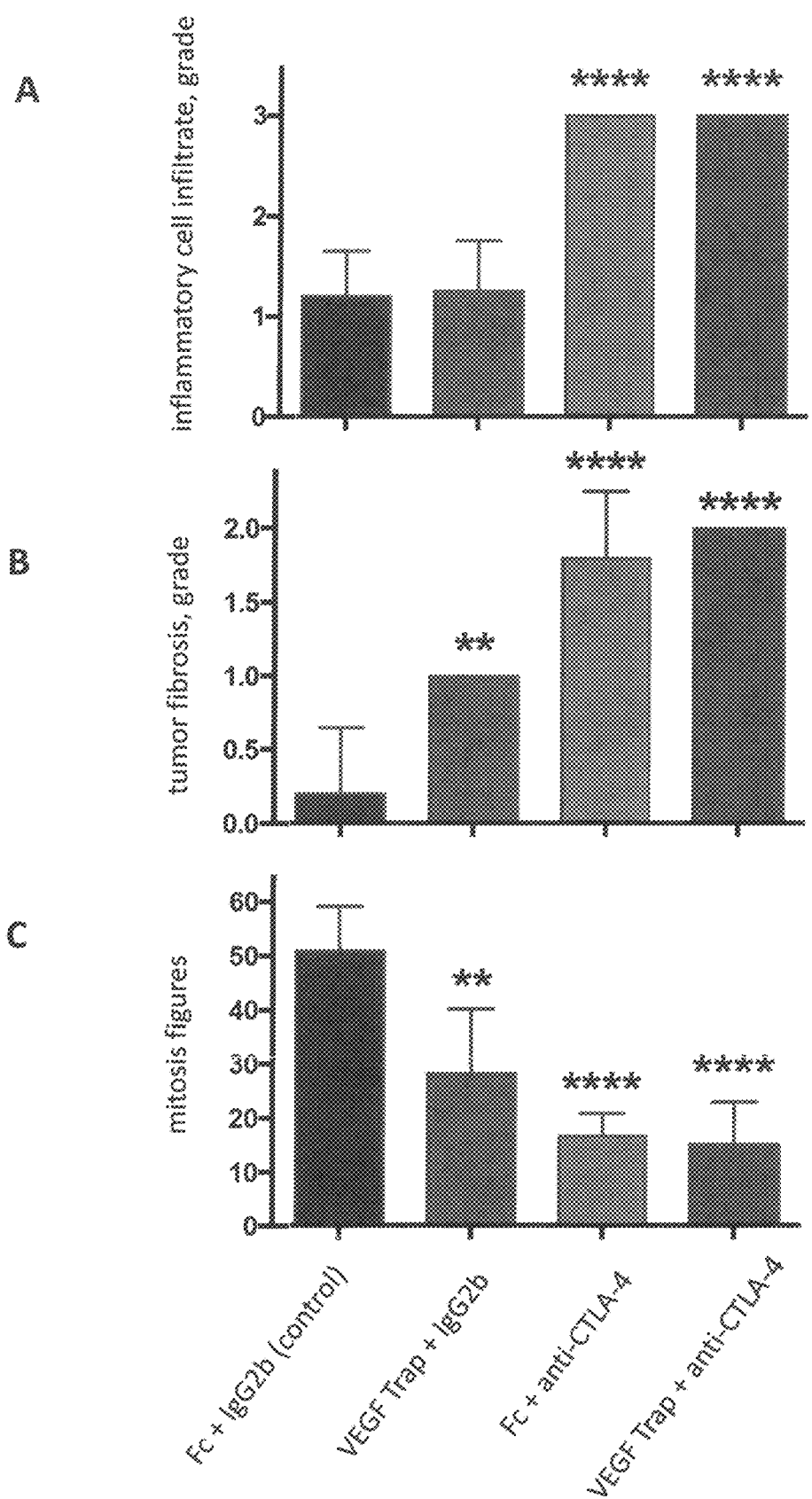

Histopathological evaluation also showed that anti-CTLA-4 treatment (alone or in combination) resulted in increased tumoral/peritumoral infiltrates composed mainly of lymphocytes and macrophages. Increased tumor necrosis, inflammatory cell infiltrates and fibrosis contributed to tumor regression in all treatment groups but were prominent in anti-CTLA-4 treated groups (FIG. 12A-C).

The results of this Example confirm that anti-CTLA-4 treatment is an effective therapeutic strategy for established tumors, and that similar therapeutic benefits are achieved with a combination of a VEGF antagonist and an anti-CTLA-4 antibody.

Example 4

Influence of Immunoglobulin Constant Region (Fc) on the Anti-Tumor Effect of Anti-CTLA-4 Antibodies, and the Enhanced Anti-Tumor Effect of VEGF Trap Combined with a High Effector Function (IgG2a) Anti-CTLA-4 Antibody In the previous Examples presented above, an anti-CTLA-4 antibody of the IgG2b isotype (i.e., the commercially available anti-mouse CTLA-4 IgG2b clone "9D9") was used in the experiments. It is known that IgG2b antibodies have low effector functions, whereas IgG2a antibodies have high effector functions. Accordingly, in this Example the role of the immunoglobulin constant region of anti-CTLA-4 antibodies was addressed. In particular, the anti-tumor effect of murine IgG2a and IgG2b versions of a mouse anti-CTLA-4 antibody were compared to one another in late-treatment mouse Colon-26 and MC38 tumor xenograft models.

In a first experiment, BalbC mice were implanted with Colon-26 tumor cells subcutaneously at $1 \times 10^6$ cells per mouse. On post-implantation day 10, mice were randomized by tumor volume (60-80 mm$^3$) into 5. The different treatment groups are summarized in Table 5.

TABLE 5

Treatment Group Descriptions

Figure 13:
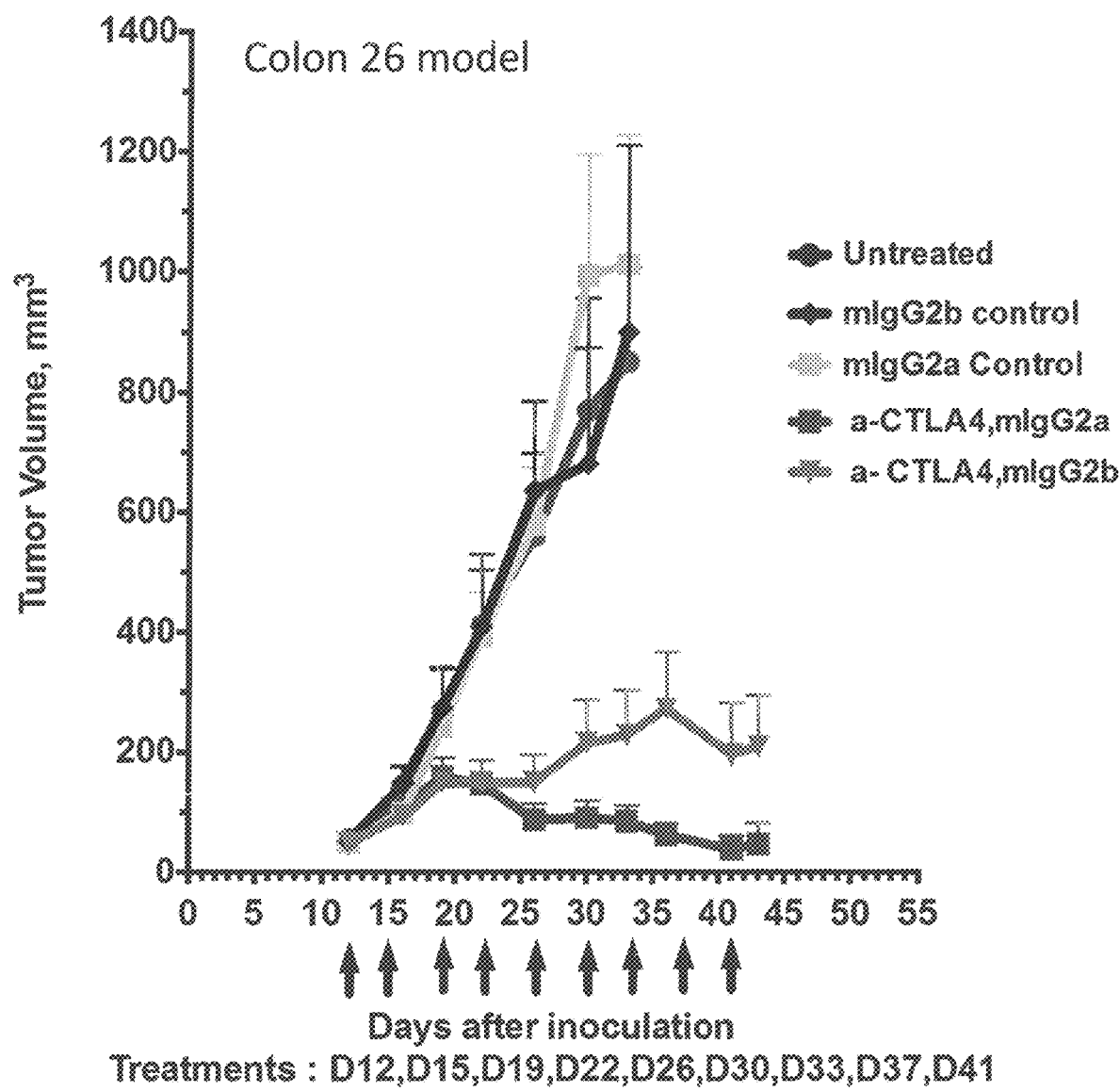
FIGS. 13 and 14 illustrate tumor growth and survival results for mice implanted with Colon-26 tumor cells at Day 0 and treated with the indicated anti-CTLA-4 antibodies (having IgG2a or IgG2b isotypes) or isotype controls following tumor establishment at Days 12, 15, 19, 22, 26, 30, 33, 37 and 41 ("late-treatment tumor model").
Figure 14:
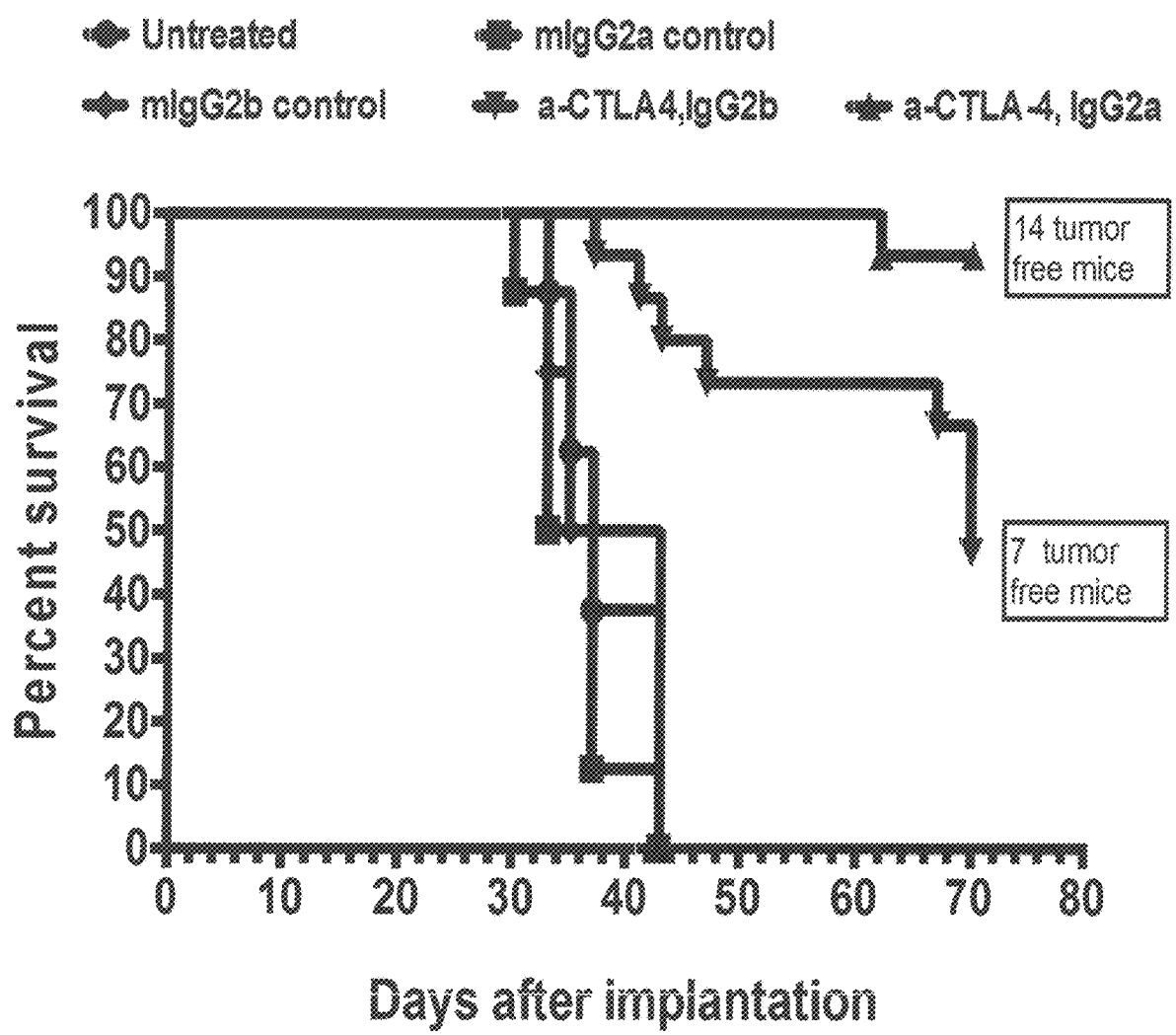

Untreated - 8 mice
Anti-CTLA-4 of mIgG2a isotype at 100 μg/mouse, IP injection - 15 mice
Anti-CTLA-4 of mIgG2b isotype (9D9) at 100 μg/mouse, IP injection - 15 mice
mIgG2a isotype control at 100 μg/mouse, IP injection - 8 mice
mIgG2b isotype control at 100 μg/mouse, IP injection - 8 mice Mice were treated on days 12, 15, 19, 22, 26, 30, 33, 37 and 41 (i.e., twice per week for the duration of the experiment) with 100 μg of anti-CTLA-4 antibody or control antibody via intraperitoneal injection (IP), as set forth in Table 5. Tumor volumes and survival were measured twice a week. Results are shown in FIGS. 13 (tumor volume) and 14 (survival).

Median survival times are shown in Table 6.

TABLE 6

| Treatment Group | Median Survival (days) |
| --- | --- |
| Untreated | 37 |
| Anti-CTLA-4 of mIgG2a isotype | >70 |
| Anti-CTLA-4 of mIgG2b isotype (9D9) | 70 |
| mIgG2a isotype control | 35 |
| mIgG2b isotype control | 39 |

In a second experiment C57/BL6 mice were implanted with MC38 tumor cells subcutaneously at $3 \times 10^6$ cells per mouse. Following implantation, after tumors reached an average size of 40-50 mm$^3$, mice were randomized into 5 different groups. The different treatment groups are summarized in Table 7.

TABLE 7

Treatment Group Descriptions

Figure 15:
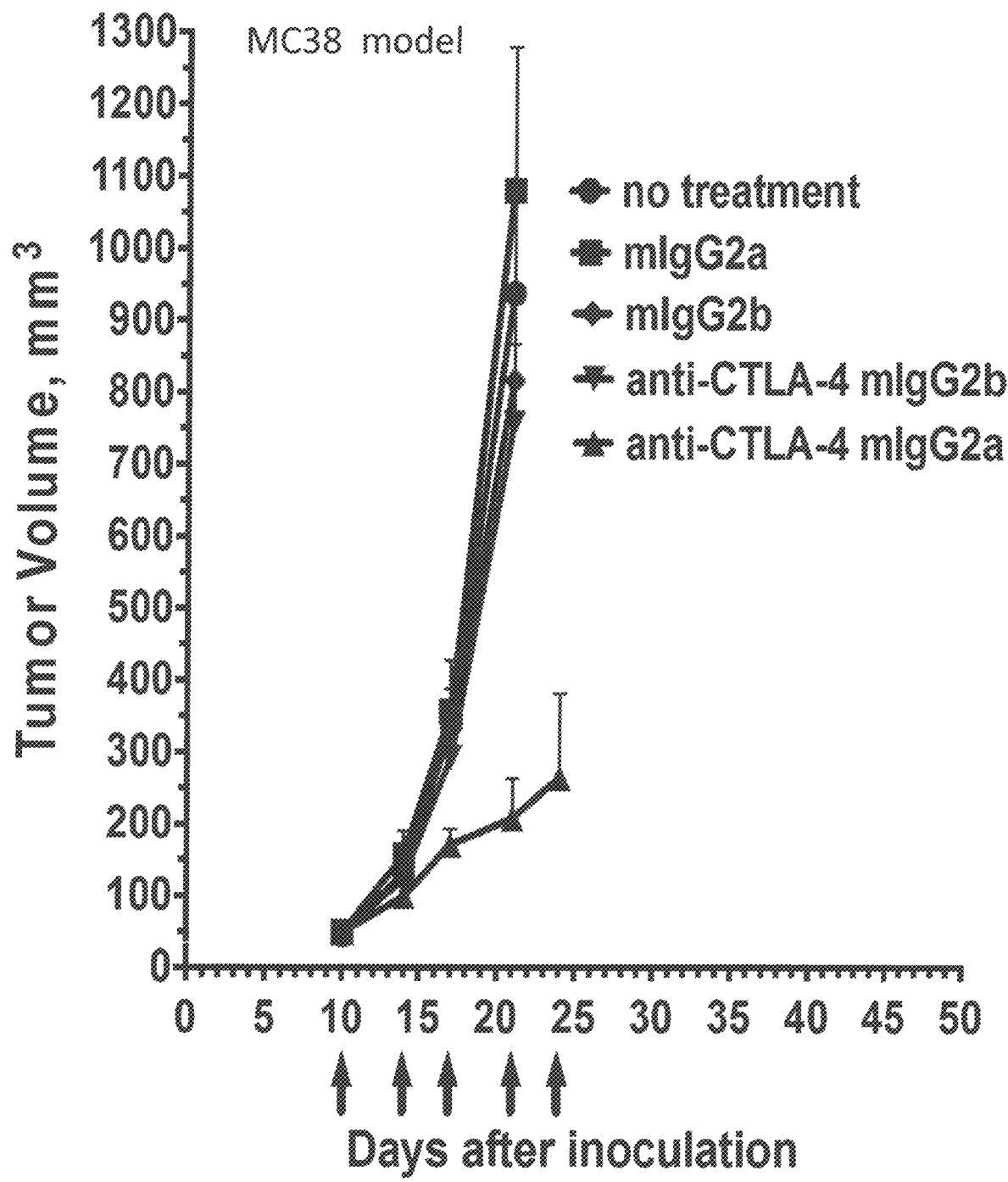
FIGS. 15-17 illustrate tumor growth and survival results for mice implanted with MC38 tumor cells at Day 0 and treated with the indicated anti-CTLA-4 antibodies (having IgG2a or IgG2b isotypes) or isotype controls following tumor establishment at Days 10, 14, 17, 21, and 24 ("late-treatment tumor model").
Figure 16:
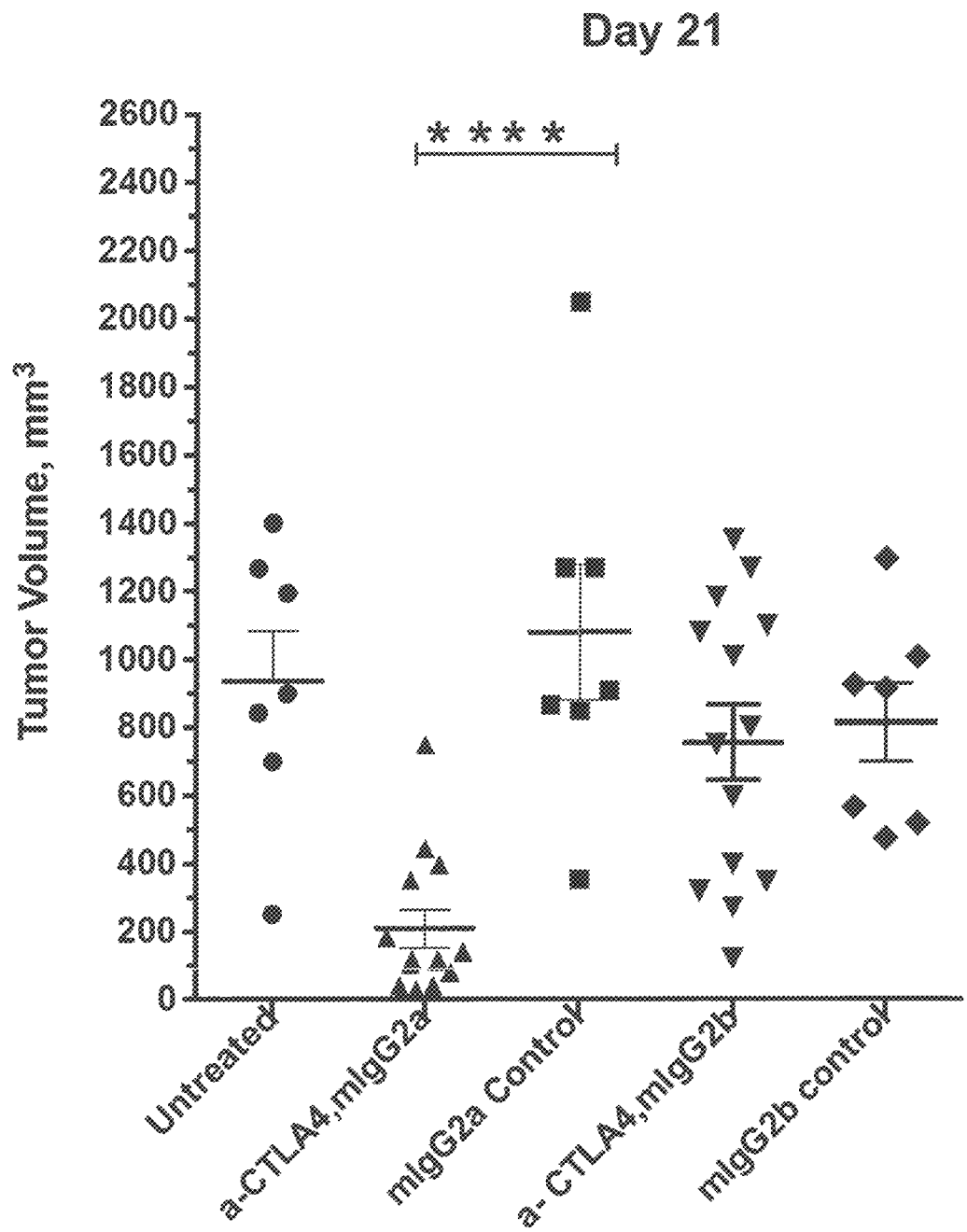
Figure 17:
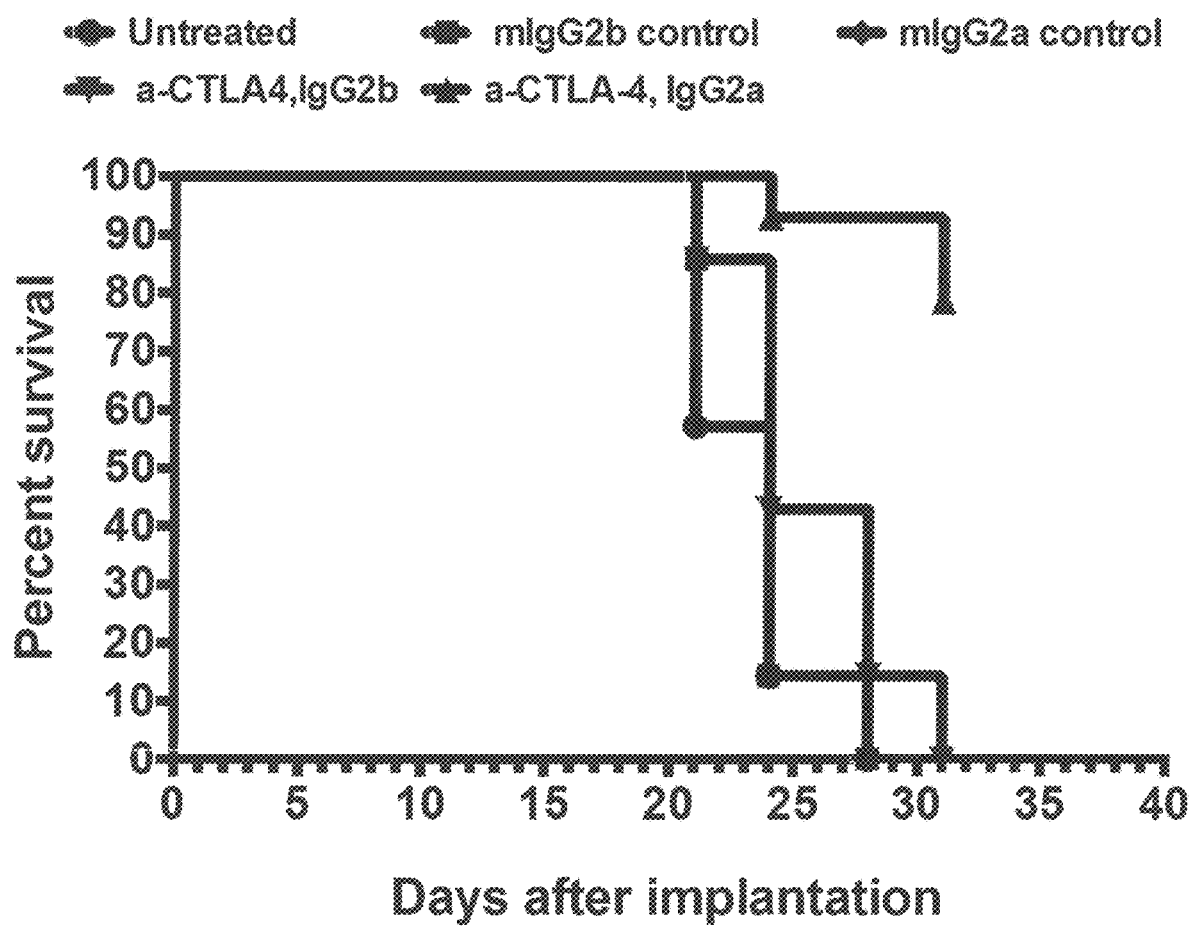

Untreated - 7 mice
Anti-CTLA-4 of mIgG2a isotype at 200 μg/mouse, IP injection - 14 mice
Anti-CTLA-4 of mIgG2b isotype (9D9) at 200 μg/mouse, IP injection - 14 mice
mIgG2a isotype control at 200 μg/mouse, IP injection - 7 mice
mIgG2b isotype control at 200 μg/mouse, IP injection - 7 mice Mice were treated on days 10, 14, 17, 21, and 24 (i.e., five injections within 2 weeks) with 200 μg of anti-CTLA-4 antibody or control antibody via intraperitoneal injection (IP), as set forth in Table 7. Tumor volumes and survival were measured twice a week. Results are shown in FIGS. 15 (tumor volume over time), 16 (tumor volume at day 21) and 17 (survival). Median survival times are shown in Table 8.

TABLE 8

| Treatment Group | Median Survival (days) |
| --- | --- |
| Untreated | 24 |
| Anti-CTLA-4 of mIgG2a isotype | >31 |
| Anti-CTLA-4 of mIgG2b isotype (9D9) | 24 |
| mIgG2a isotype control | 24 |
| mIgG2b isotype control | 24 |

The results of these experiments demonstrated that the anti-CTLA-4 IgG2a antibody was significantly more potent than the IgG2b version, resulting in eradication of established Colon-26 tumors and partial growth inhibition of established MC38 tumors. By contrast, these established tumors were resistant to IgG2b therapy.

In a third experiment, the antitumor effect of a combination of an anti-CTLA-4 mIgG2a antibody and VEGF Trap was investigated in vivo. In this experiment, mice were implanted with MC38 tumor cells subcutaneously at $3 \times 10^5$ cells per mouse on Day 0. Following implantation, after tumors reached an average size of 60-80 mm$^3$ (on Day 14), mice were randomized into 4 different groups. The different treatment groups are summarized in Table 9.

TABLE 9

| Treatment Group | First Agent | Second Agent |
| --- | --- | --- |
| Control Combination | IgG2a isotype control (200 µg, IP) | hFc control (10 mg/kg SC) |
| VEGF Trap only | IgG2a isotype control (200 µg, IP) | Aflibercept (10 mg/kg, SC) |
| anti-CTLA-4 only | anti-CTLA-4 IgG2a mAb (200 µg, IP) | hFc control (10 mg/kg SC) |
| VEGF Trap + anti-CTLA-4 | anti-CTLA-4 IgG2a mAb (200 µg, IP) | Aflibercept (10 mg/kg, SC) |

Figure 18:
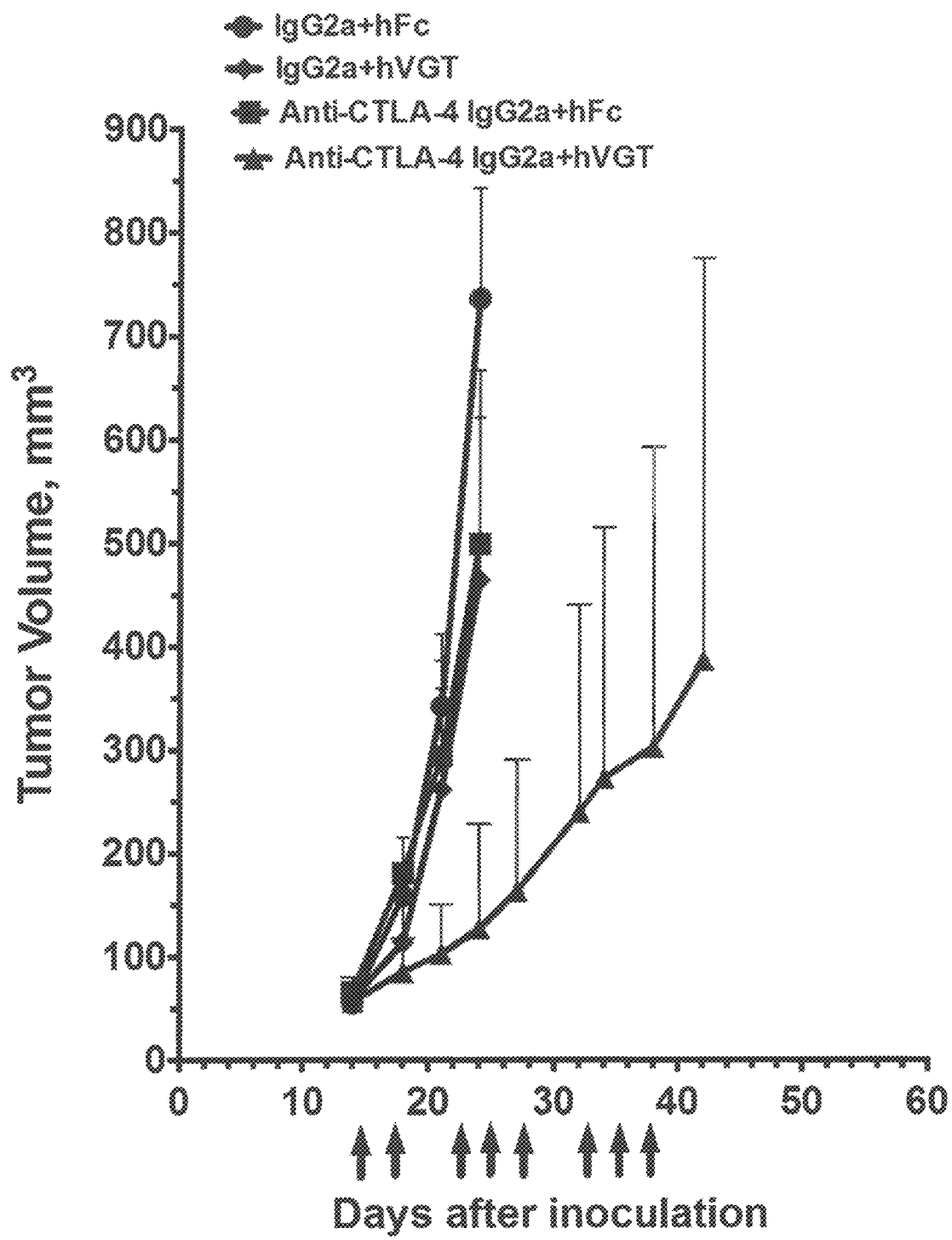
FIGS. 18 and 19 illustrate tumor growth results for mice implanted with MC38 tumor cells at Day 0 and treated with the indicated combinations of molecules by injection at Days 15, 17, 23, 25, 27, 33, 35 and 37 ("late-treatment tumor model").
Figure 19:
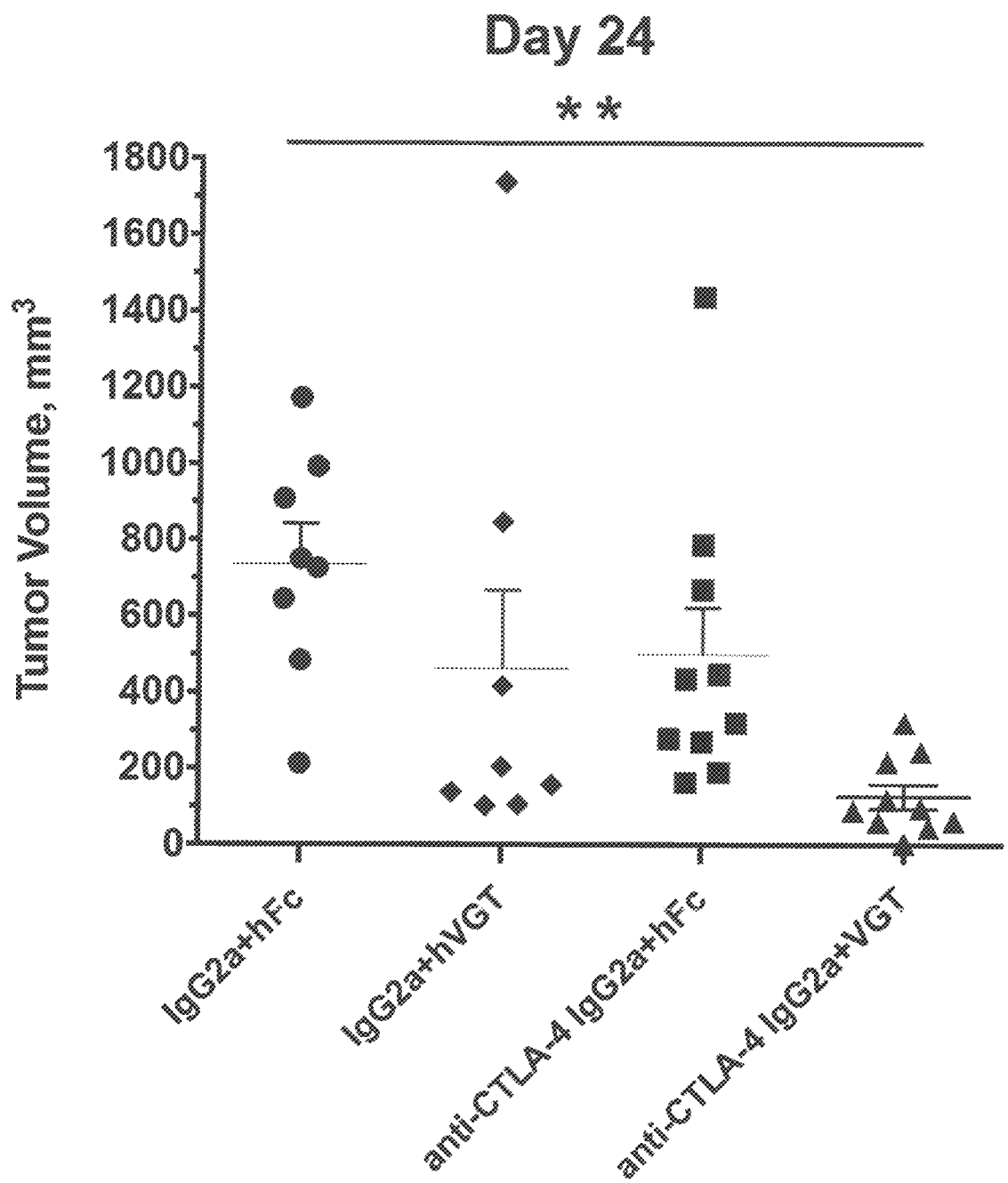

Mice were treated with the control and experimental combinations on days 15, 17, 23, 25, 27, 33, 35 and 37 via intraperitoneal injection (IP), as set forth in Table 9. Tumor volumes were measured twice a week. Results are shown in FIGS. 18 (tumor volume over time), and 19 (tumor volume at day 24).

In a fourth experiment, the antitumor effect of a combination of an anti-CTLA-4 mIgG2b antibody and VEGF Trap was investigated in vivo. In this experiment, mice were implanted with MC38 tumor cells subcutaneously at $3 \times 10^5$ cells per mouse on Day 0. Following implantation, after tumors reached an average size of 60-80 mm³ (on Day 10), mice were randomized into 4 different groups. The different treatment groups are summarized in Table 10.

TABLE 10

| Treatment Group | First Agent | Second Agent |
| --- | --- | --- |
| Control Combination | IgG2b isotype control (200 µg, IP) | hFc control (10 mg/kg SC) |
| VEGF Trap only | IgG2b isotype control (200 µg, IP) | Aflibercept (10 mg/kg, SC) |
| anti-CTLA-4 only | anti-CTLA-4 IgG2b mAb (200 µg, IP) | hFc control (10 mg/kg SC) |
| VEGF Trap + anti-CTLA-4 | anti-CTLA-4 IgG2b mAb (200 µg, IP) | Aflibercept (10 mg/kg, SC) |

Figure 20:
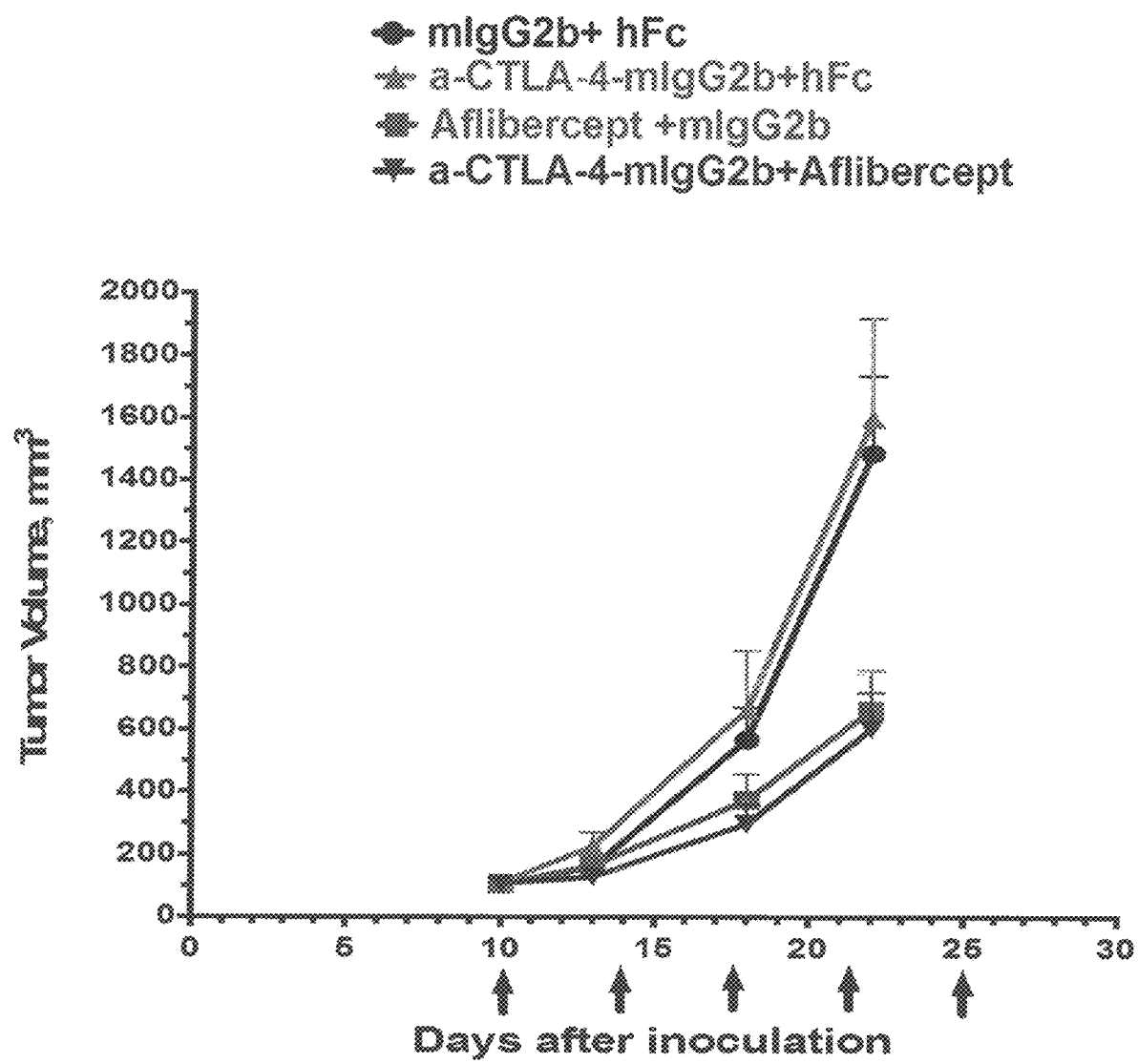
FIGS. 20 and 21 illustrate tumor growth results for mice implanted with MC38 tumor cells at Day 0 and treated with the indicated combinations of molecules by injection at Days 10, 14, 18, 21 and 25 ("late-treatment tumor model").
Figure 21:
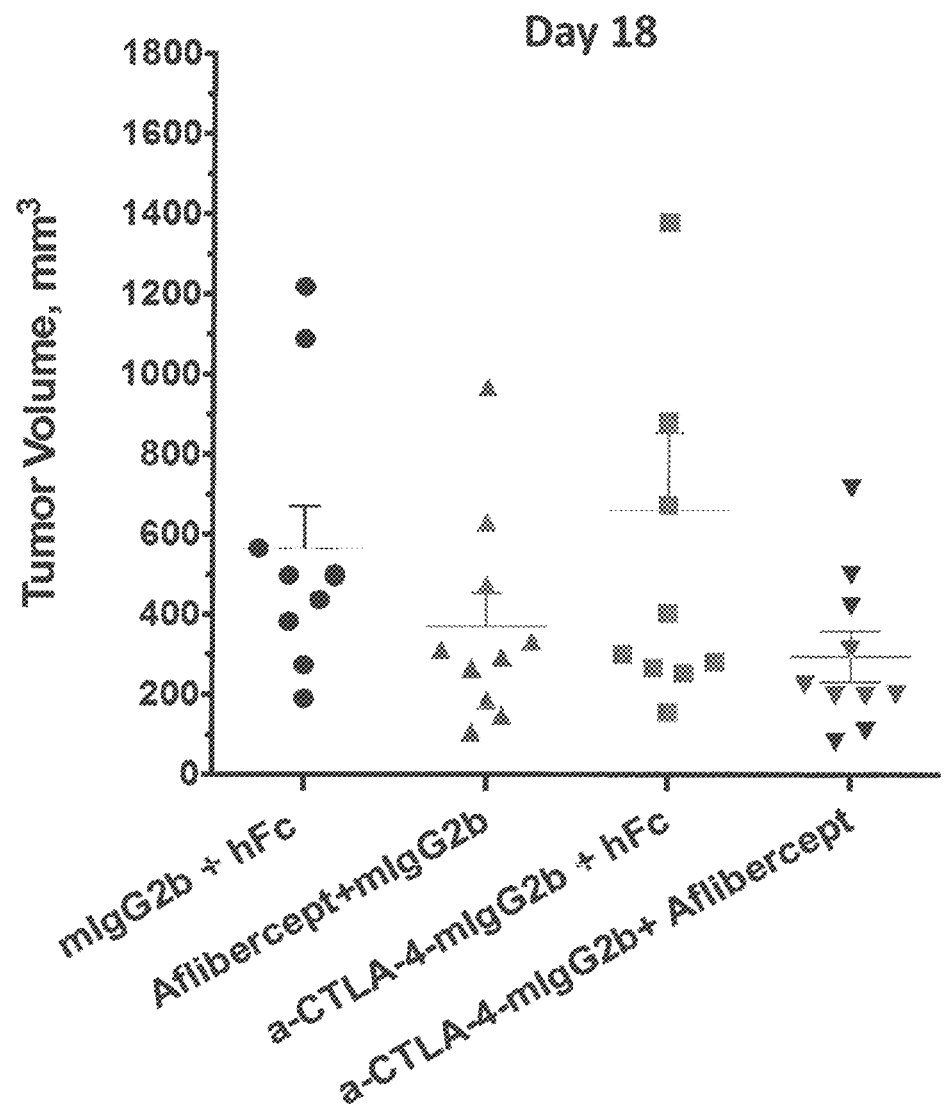

Mice were treated with the control and experimental combinations on days 10, 14, 18, 21, and 25 via intraperitoneal injection (IP), as set forth in Table 10. Tumor volumes were measured twice a week. Results are shown in FIGS. 20 (tumor volume over time), and 21 (tumor volume at day 18).

Importantly, as shown in the third and fourth experiments set forth above, anti-CTLA-4 IgG2a antibody and VEGF Trap (aflibercept) have robust combination effects in established MC38 tumors, whereas anti-CTLA4 IgG2b antibody does not potentiate VEGF Trap efficacy. These results provide additional evidence that combining immunotherapy (e.g., anti-CTLA-4 treatment) and VEGF antagonism may be beneficial for the treatment of established tumors in a clinical setting.

Example 5

Quantitative Assessment of T Cell Infiltration, Activated Immunity, and Neovascularization in Mice Treated with a Combination of an Anti-CTLA4 Antibody and VEGF Trap In this Example, the effects of combined VEGF-Trap and anti-CTLA-4 antibody treatment on tumor growth and other quantitative gene expression and tumor infiltration-related parameters were examined in an established MC38 mouse carcinoma subcutaneous tumor model.

Syngeneic 057/B16 mice at 8-10 weeks of age were engrafted in the right flank with a 100 µl suspension of $3 \times 10^5$ MC38 cells on day 0. On day 9, mice with established tumors were randomized into groups (n=8 mice/group) with average tumor volume 50 mm³, and administered four treatments of anti-CTLA-4 antibody (anti-mouse CTLA4, clone 9D9 with a mIgG2a isotype), VEGF-Trap (VEGFR1R2-FcΔC1(a)), a combination of anti-CTLA-4 antibody and VEGF-Trap, or isotype controls, on days 9, 13, 16 and 20. VEGF-Trap and hFc control were dosed subcutaneously at 10 mg/kg, and anti-CTLA-4 antibody and mIgG2a isotype control were dosed i.p. at 200 µg per mouse.

Tumor size (volume in mm³) was measured by electric caliper at various time points throughout the course of the experiment.

On day 21, mice were sacrificed and tumors were removed for quantitative real-time polymerase chain reaction (PCR) analysis of mRNA of specific genes (Taqman®).

Total RNA was purified from tissues using MagMAX™-96 for Microarrays Total RNA Isolation Kit (Ambion by Life Technologies) according to manufacturer's specifications. Genomic DNA was removed using MagMAX™ Turbo™ DNase Buffer and TURBO DNase from the MagMAX kit listed above (Ambion by Life Technologies). mRNA was reverse-transcribed into cDNA using SuperScript® VILO™ Master Mix (Invitrogen by Life Technologies). cDNA was diluted to 5 ng/µL and 25 ng and cDNA was amplified with the TaqMan® Gene Expression Master Mix (Applied Biosystems by Life Technologies) using the ABI 7900HT Sequence Detection System (Applied Biosystems). Cyclophilin B (Ppib) was used as the internal endogenous control gene to normalize any cDNA input differences. FAM dye-labeled Taqman MGB probe (Life Technologies) was used for mouse CD247 (Mm00446171_m1), mIFNγ (Mm01168134_m1), mTNFα (Mm00443260_g1), mDll4 (Mm01338015_m1), mAng2 (Mm00545822_m1), mRobo4 (Mm00452963_m1), mItgam (Mm00434455_m1), mEmr1 (Mm00802529_m1), mItgax (Mm00498701_m1), E-selectin (Mm01310197_m1). FAM dye labeled BHQ1 probe (Biosearch Technologies) was used for mouse CD8b. The PCR thermal cycle conditions were as follows: initial step at 95° C. for 10 min, followed by 40 cycles of 95° C. for 3 s and 60° C. for 30 s. The ratio of the mRNA level of each gene was calculated as follows: (absolute copy number of each gene)/(absolute copy number of cyclophilin B).

Results are expressed as mean values +/− standard error, and ordinary one-way ANOVA with Tukey's multiple comparisons test was used to evaluate statistical significance. A value less than 0.05 was considered statistically significant. *P<0.05; P<0.005; *P<0.0005; ****P<0.0001.

Figure 22:
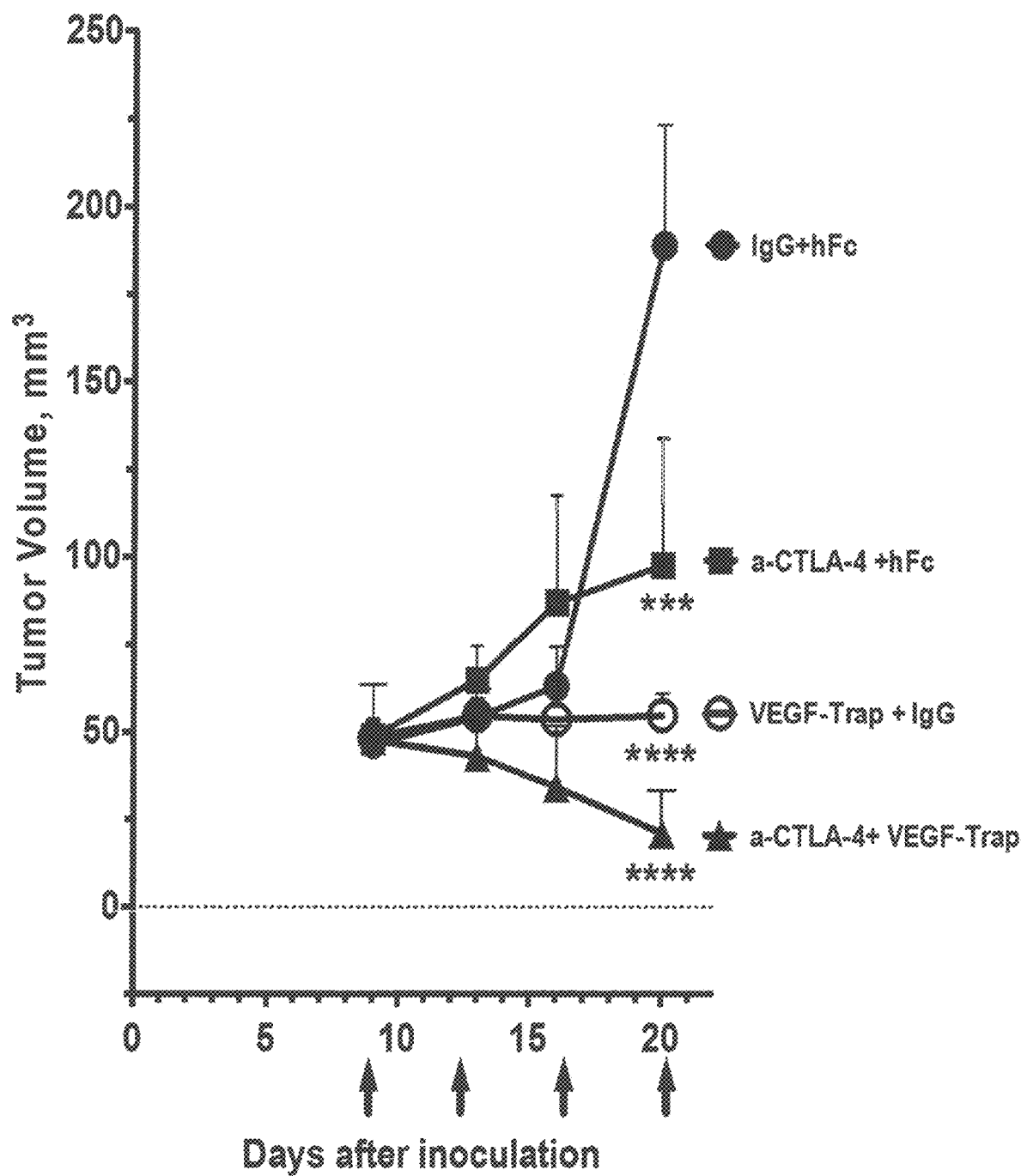
FIG. 22 illustrates tumor growth results (tumor volume [in $mm^3$]) for mice implanted with MC38 tumor cells at Day 0 and treated with the indicated combinations of molecules by injection at Days 9, 13, 16 and 20 ("late-treatment tumor model").

In vivo treatment of established MC38 tumors with either anti-CTLA-4 antibody or VEGF-Trap resulted in significant inhibition of tumor growth compared to the control (FIG. 22, closed squares ■, and open circles ○, respectively). Blockade with both agents further reduced MC38 tumor growth, showing combination anti-tumor effect (FIG. 22, closed triangles ▲).

Figure 23:
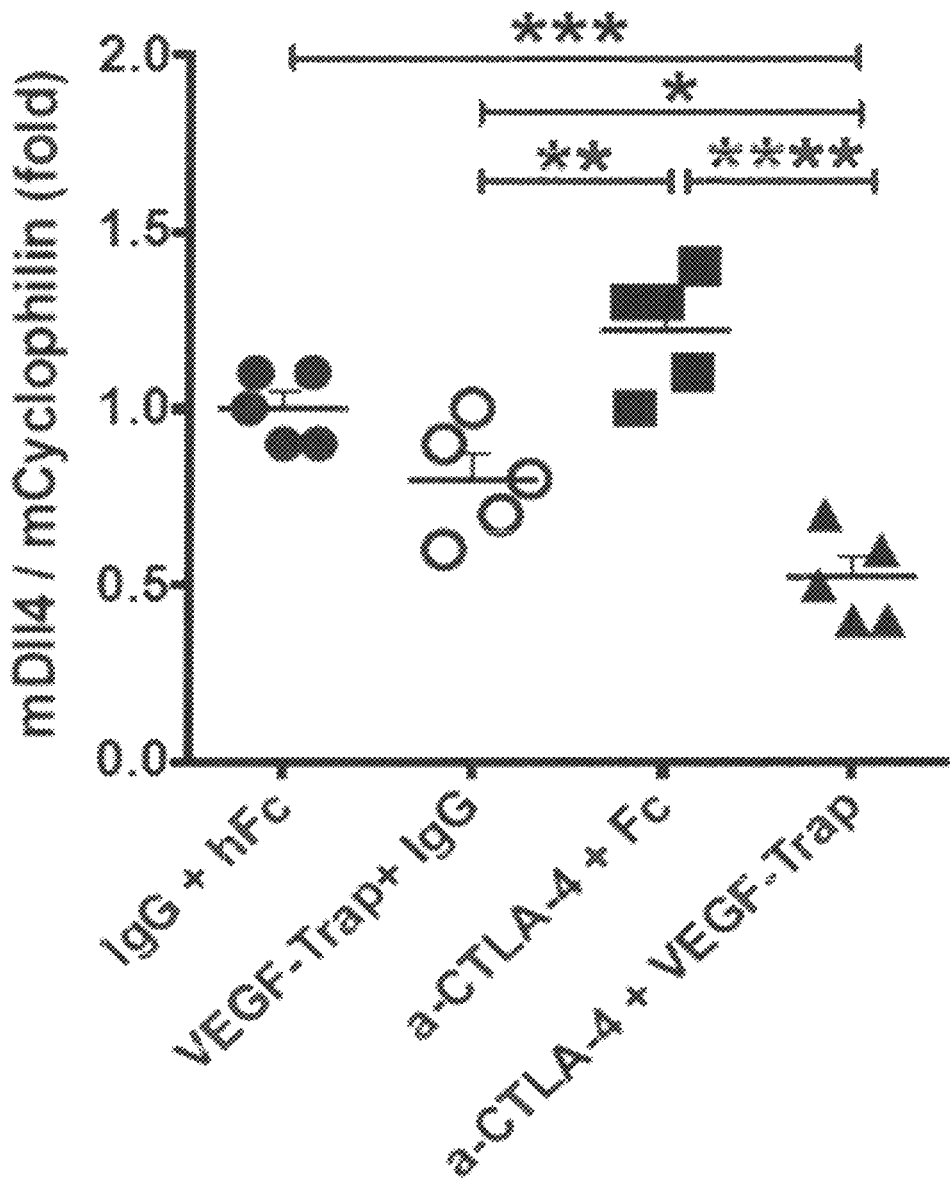
FIGS. 23, 24 and 25 depict the relative levels of expression of angiogenic marker genes Dll4 (FIG. 23), Ang2 (FIG. 24), and Robo4 (FIG. 25), as measured by real-time PCR analysis of established tumors obtained from mice following treatments with the indicated combinations of molecules.
Figure 24:
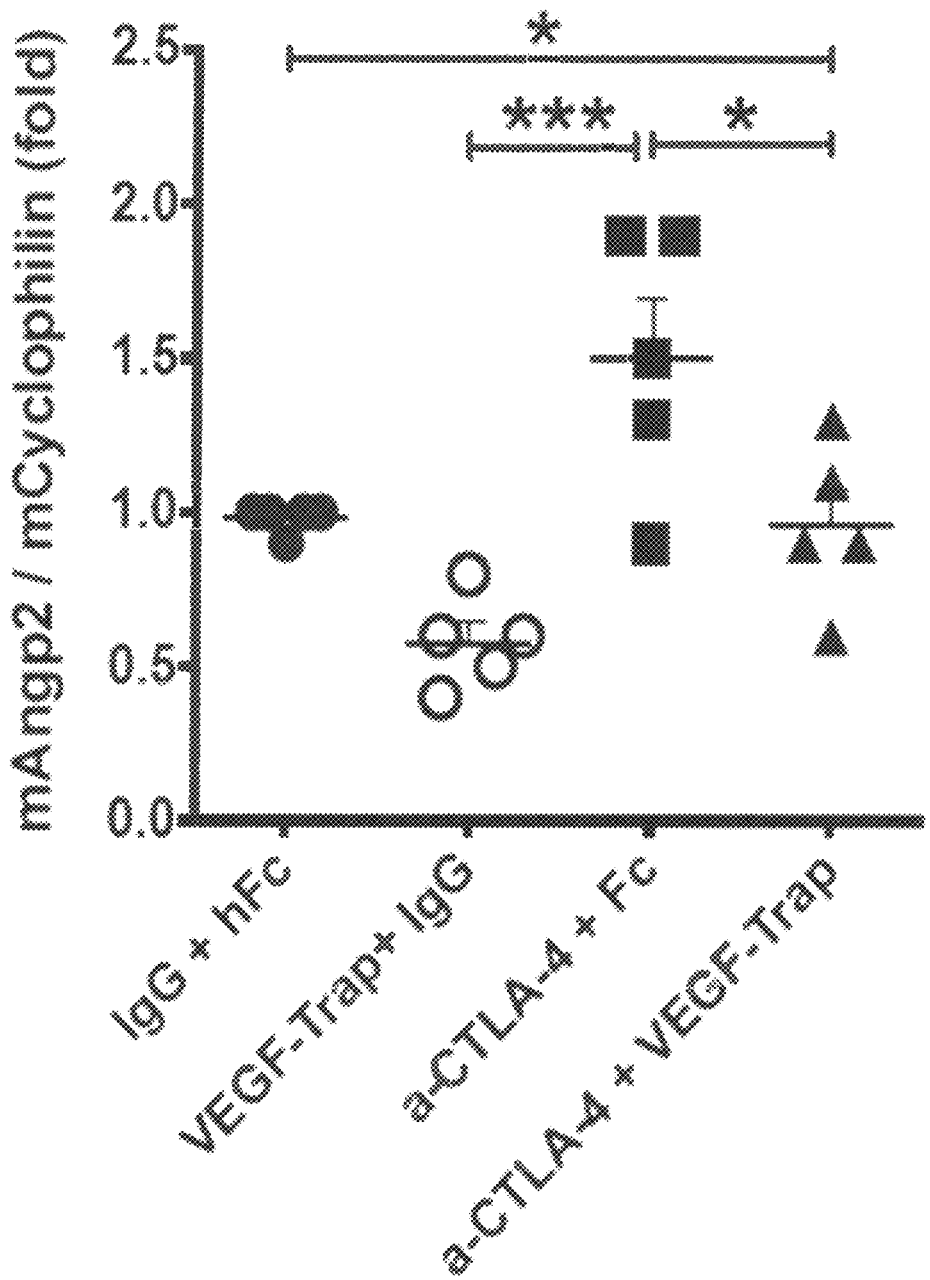
Figure 25:
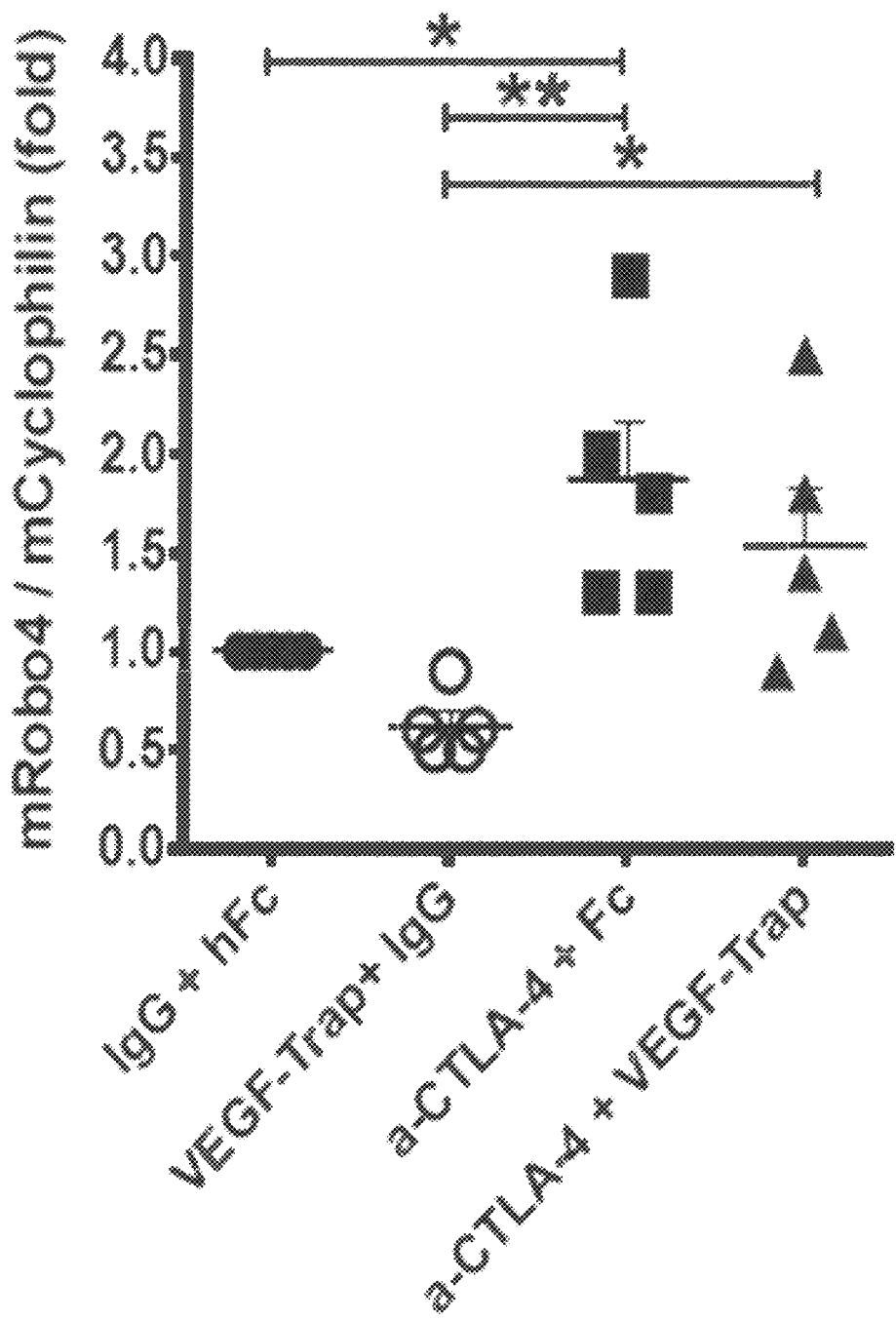
Figure 26:
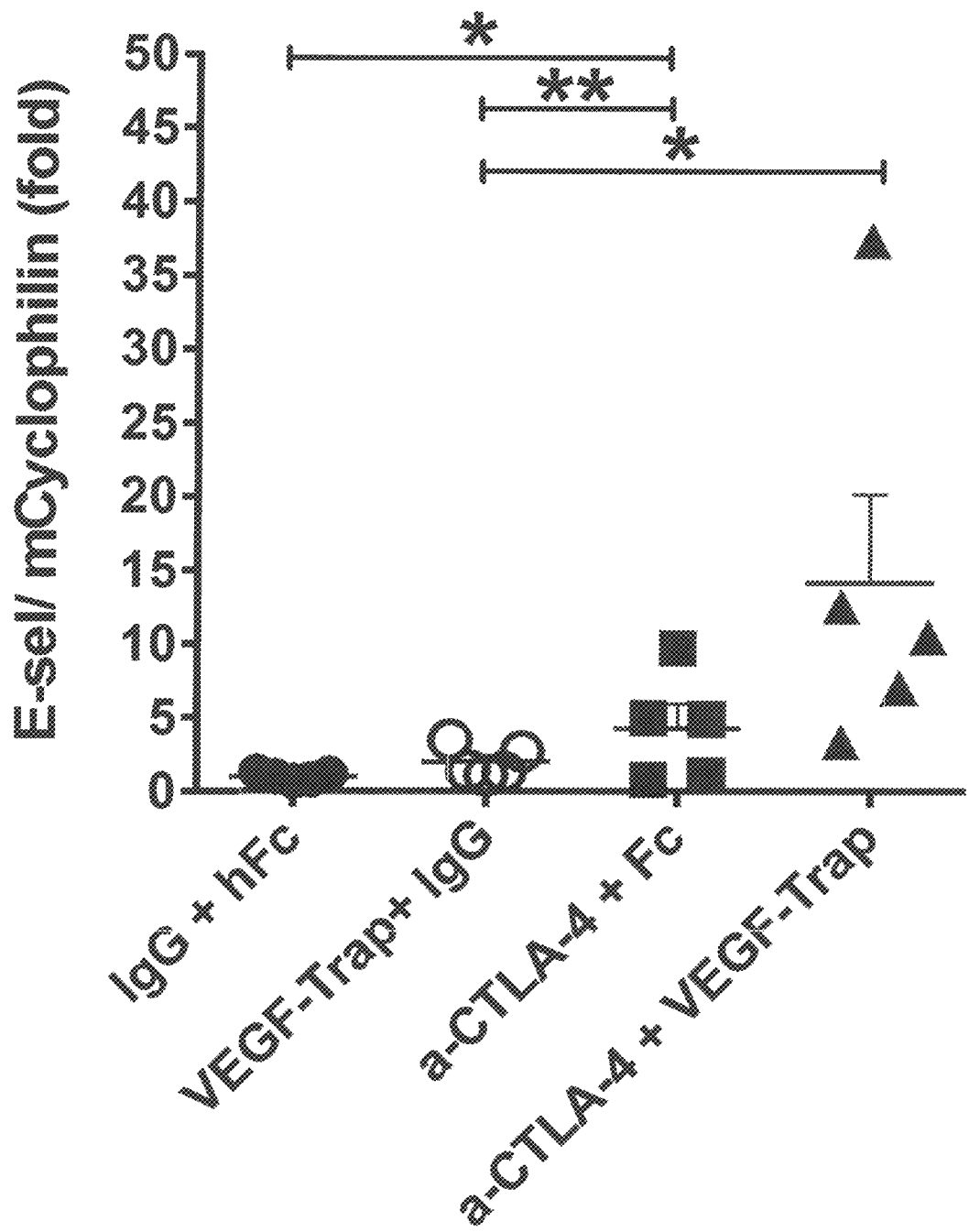
FIG. 26 depicts the relative level of expression of E-selectin as measured by real-time PCR analysis of established tumors obtained from mice following treatments with the indicated combinations of molecules.

Real time PCR analysis of tumor RNA has revealed that the anti-angiogenic agent VEGF-Trap down-regulates expression of angiogenic marker genes Dll4, Ang2 and Robo4, whereas anti-CTLA-4 therapy did not affect these genes. (FIGS. 23, 24 and 25, respectively). VEGF-Trap combination with anti-CTLA-4 Ab significantly increased the level of E-selectin (FIG. 26) indicating endothelial cell activation, which reflect improved ability of lymphocytes to migrate to tumors.

Figure 27:
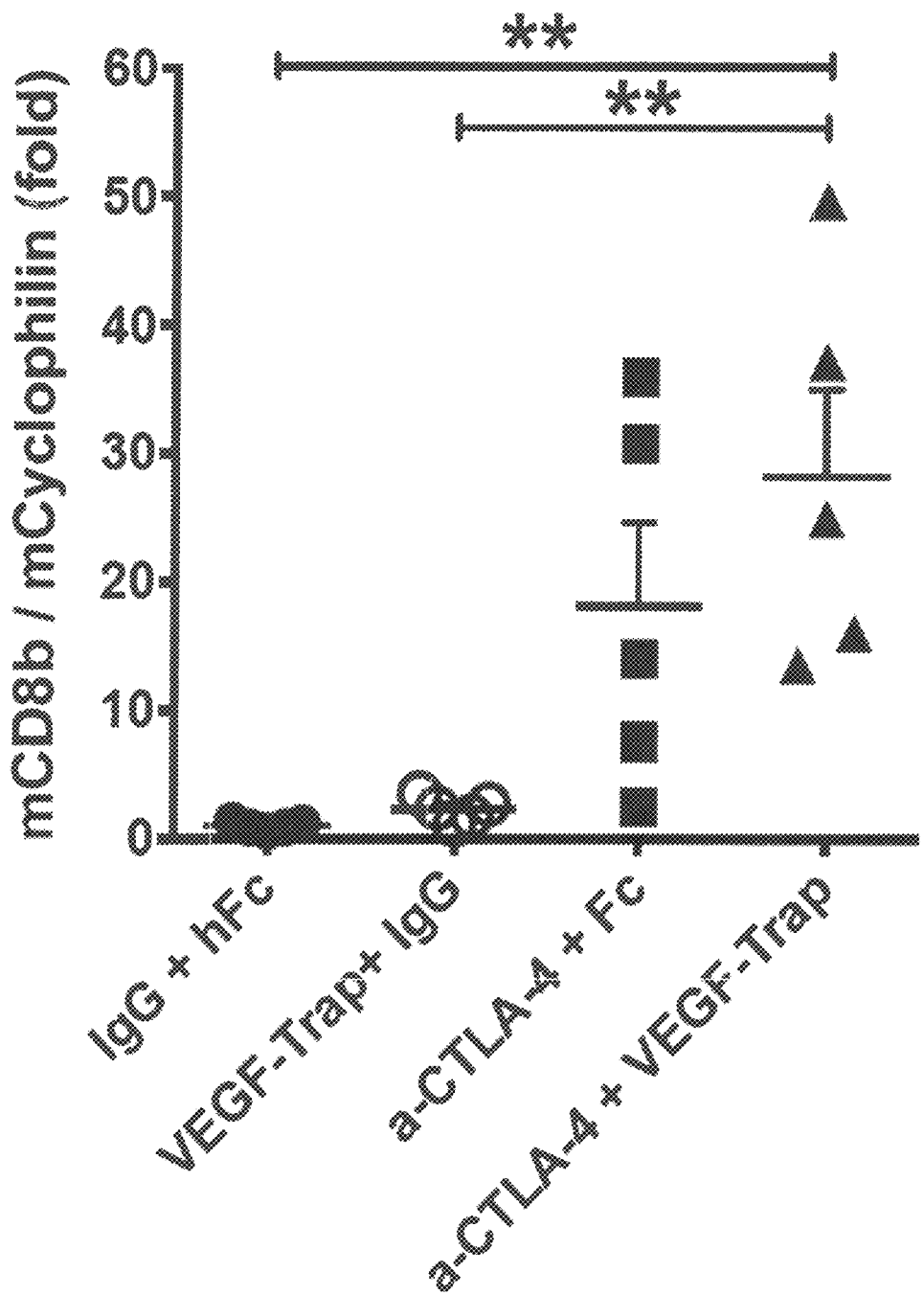
FIGS. 27 and 28 depict the relative levels of expression of CD8 and CD247, respectively, as measured by real-time PCR analysis of established tumors obtained from mice following treatments with the indicated combinations of molecules; the expression of which reflect the level of expression of tumor-infiltrating lymphocytes in the various treatment groups.
Figure 28:
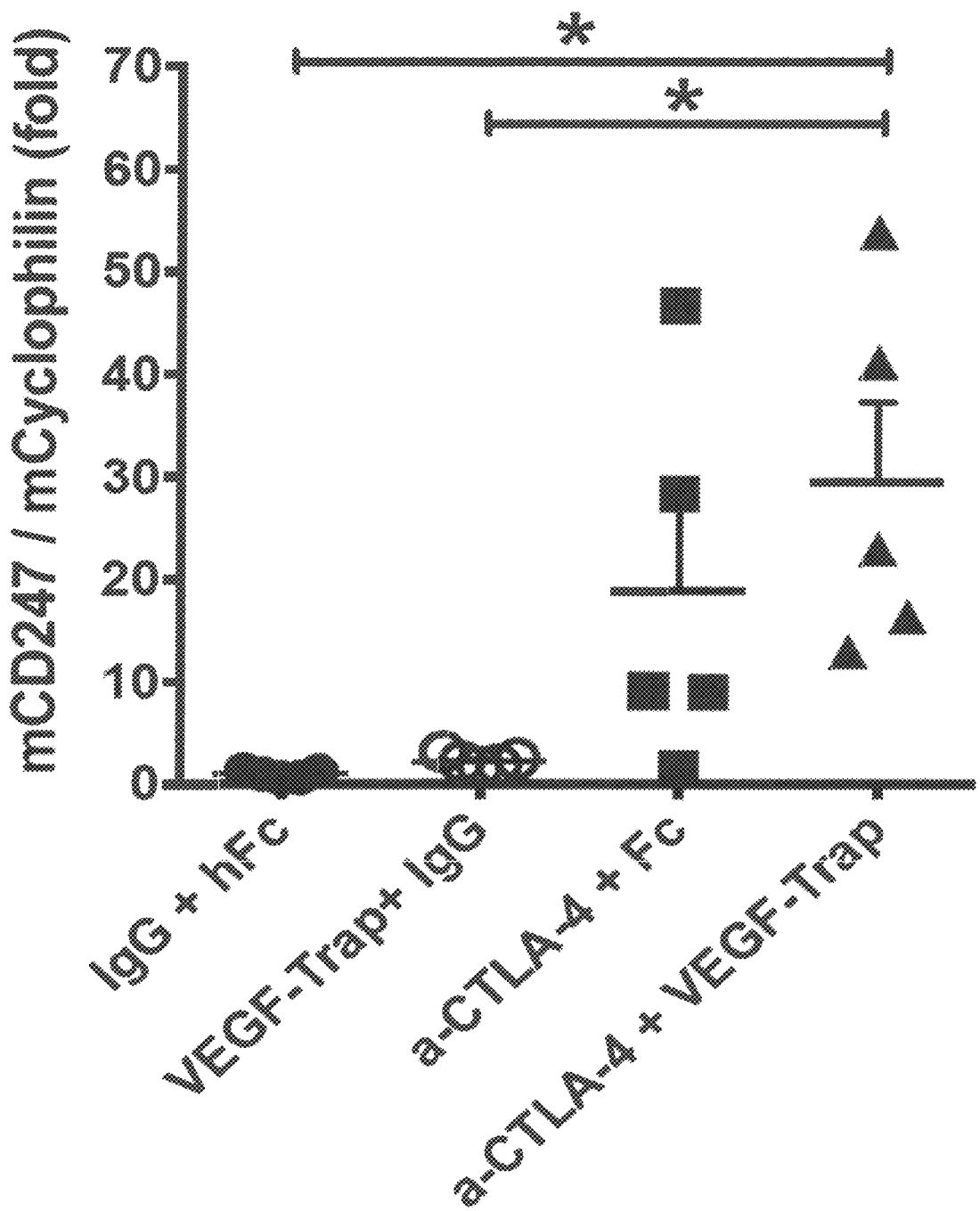

Real time PCR analysis was also used to evaluate expression of tumor infiltrating lymphocytes in order to assess anti-tumor immune responses. Although VEGF-Trap did not affect T lymphocyte recruitment, anti-CTLA-4 Ab therapy substantially increased the number of CD8+ and CD3+ T cells (CD247), which were further increased in the combination group (FIGS. 27 and 28). Treatment with anti-CTLA4 Ab, but not with VEGF-Trap, also resulted in increased expression of Treg cell marker forkhead box protein 3 (FoxP3) (not shown).

Figure 29:
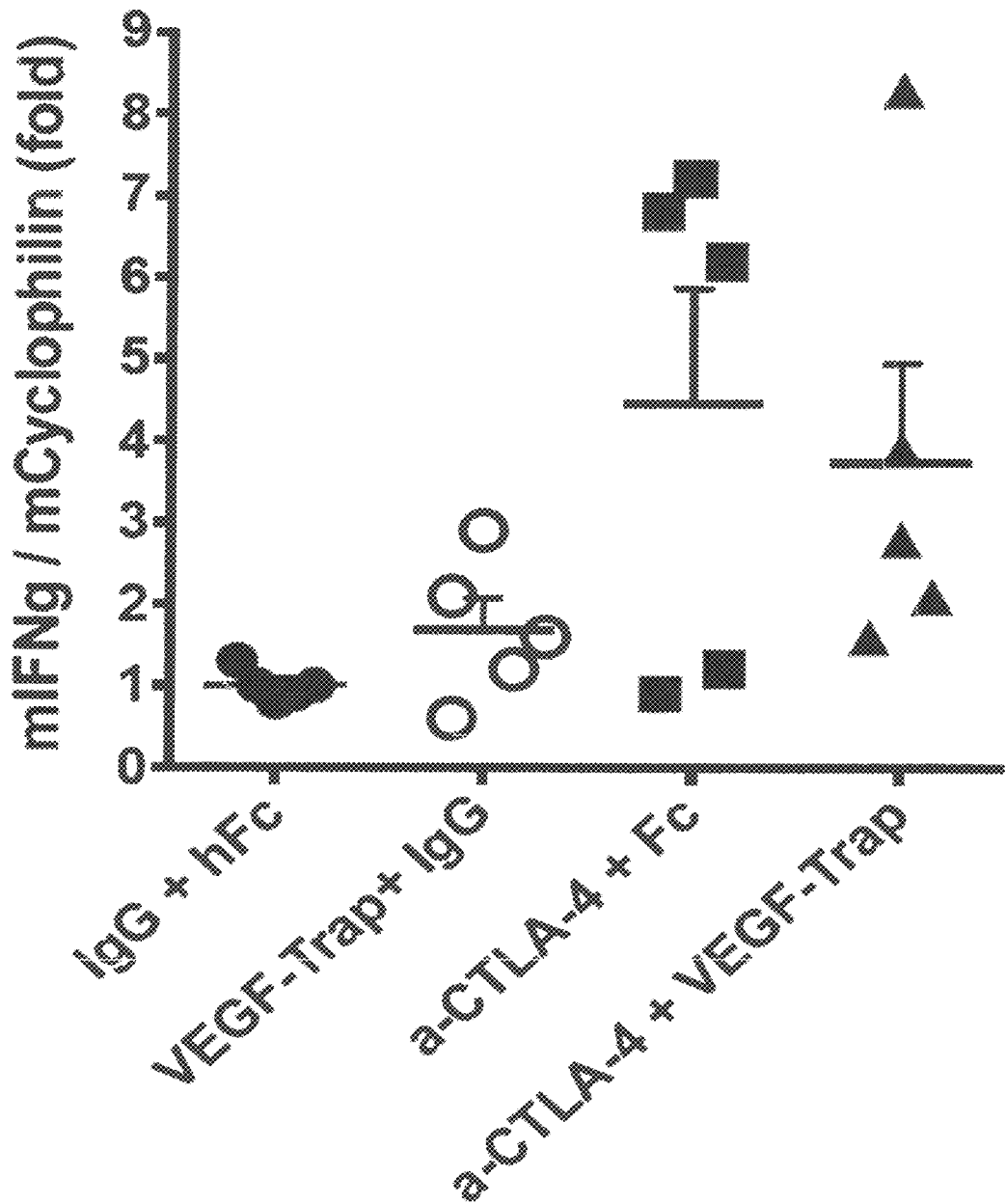
FIGS. 29 and 30 depict the relative levels of expression of inflammatory cytokines IFNγ and TNFα, respectively, as measured by real-time PCR analysis of established tumors obtained from mice following treatments with the indicated combinations of molecules.
Figure 30:
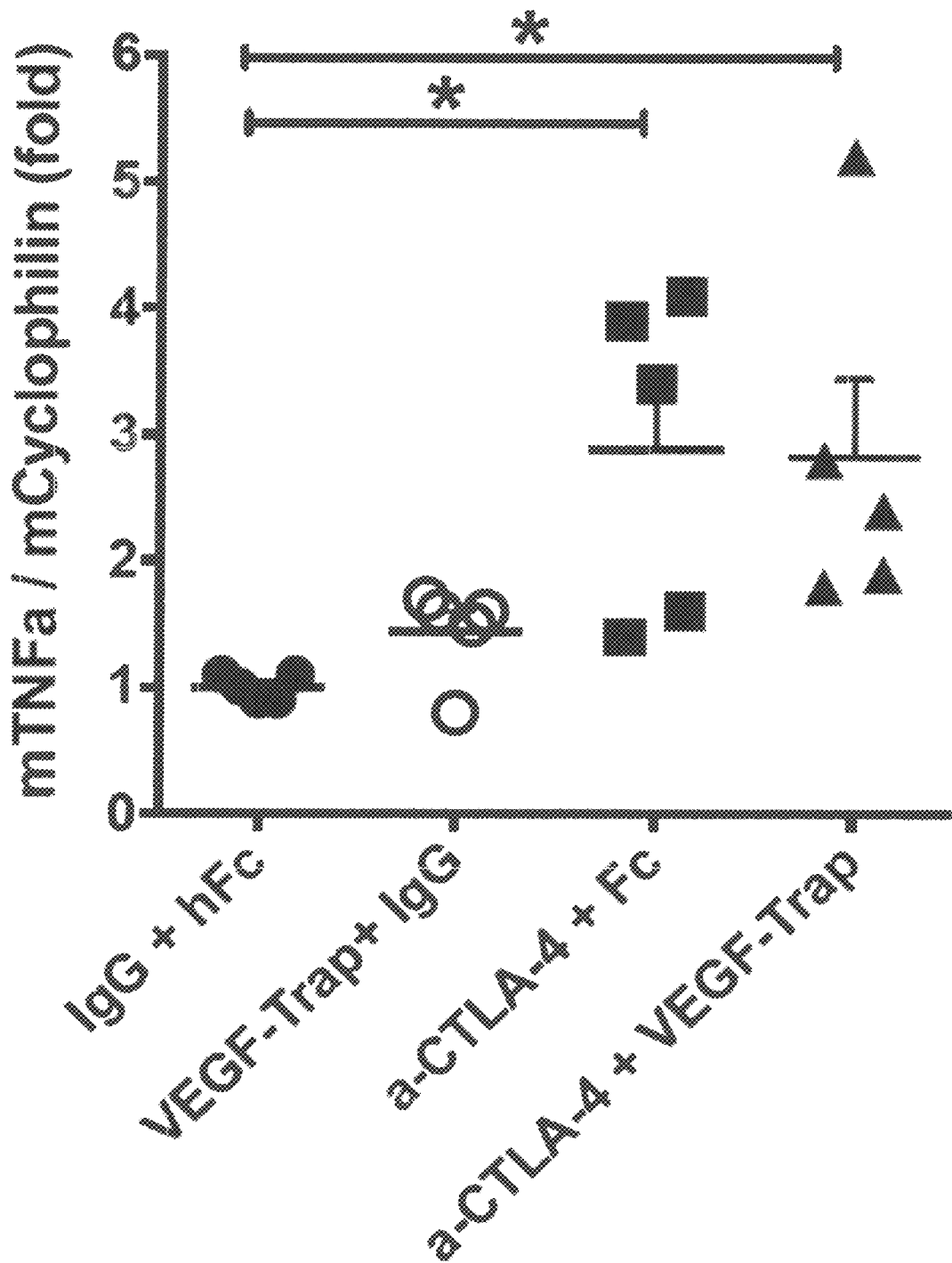

Tumor immune environment was further analyzed by evaluating expression of inflammatory cytokines. Anti-CTLA4 antibody and the combination therapies significantly increased the levels of interferon (IFNγ) and tumor necrosis factor (TNFα), whereas VEGF-Trap monotherapy had neither of these effects (FIGS. 29 and 30, respectively).

Figure 31:
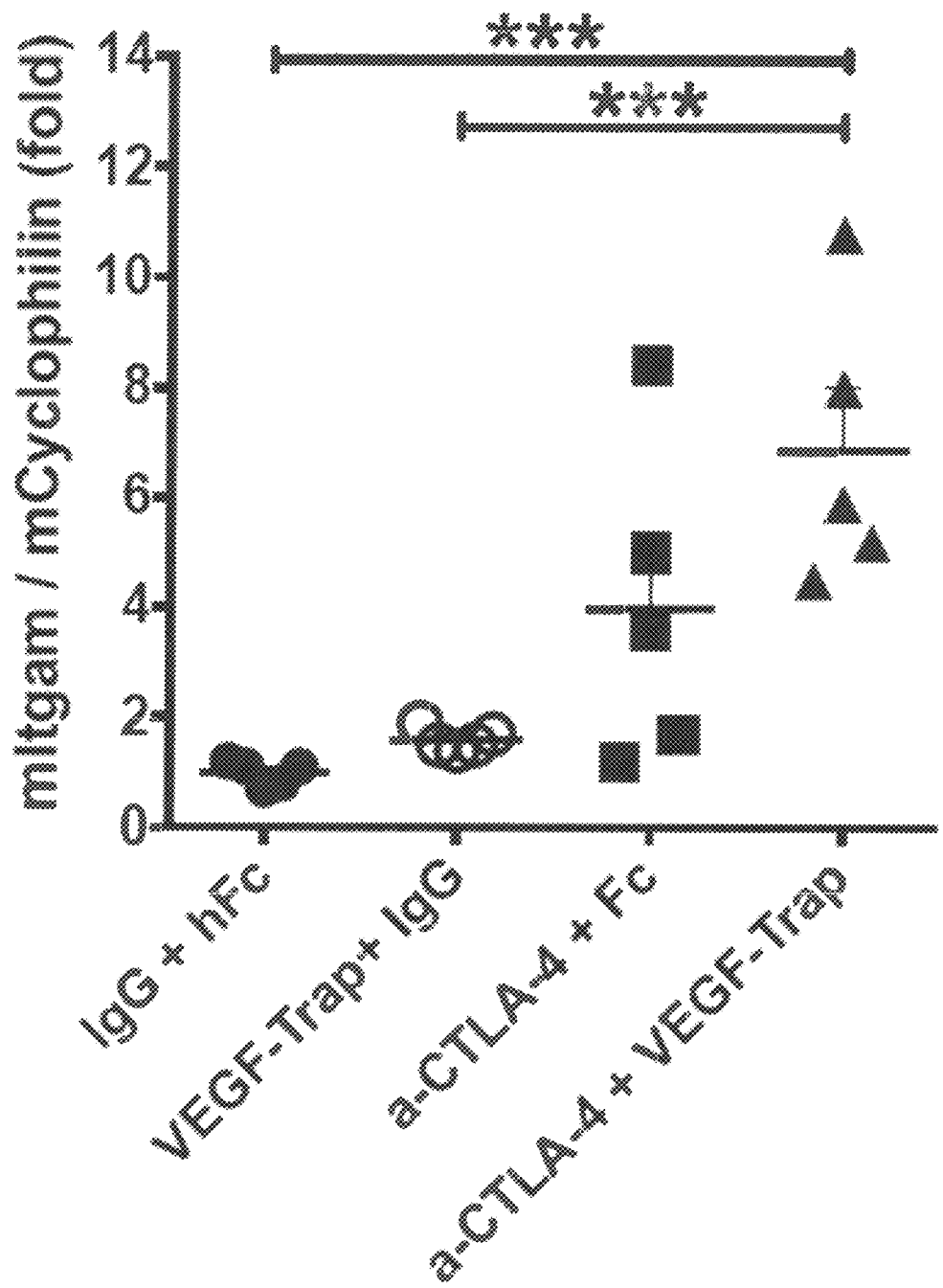
FIGS. 31, 32 and 33 depict the relative levels of expression of Itgam (CD11b), Emr1 (F4/80) and Itgax (CD11c), respectively, as measured by real-time PCR analysis of established tumors obtained from mice following treatments with the indicated combinations of molecules; the expression of which reflect the level of myeloid cell infiltrates (myeloid cells, macrophages and dendritic cells, respectively) in the various treatment groups.
Figure 32:
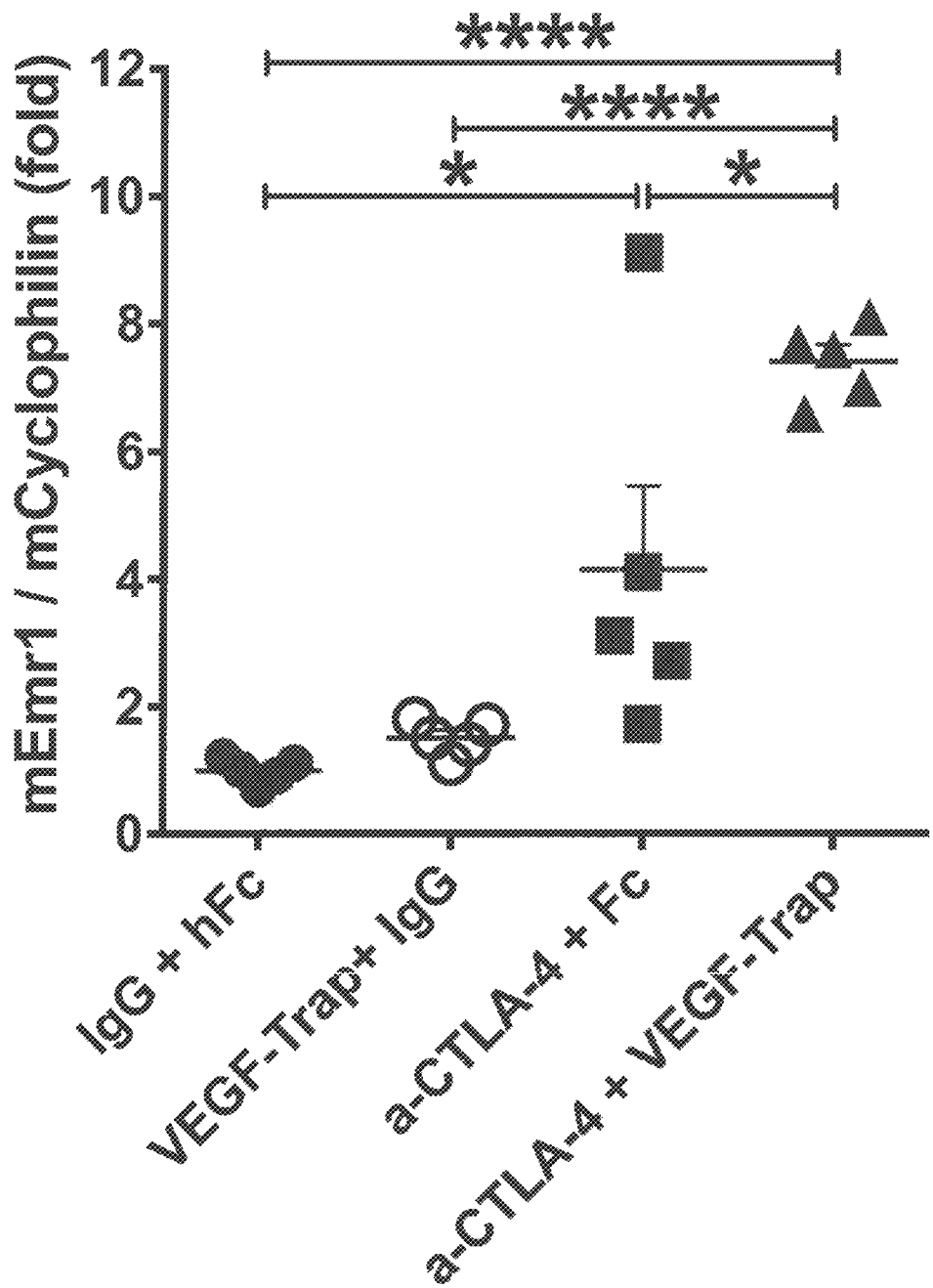
Figure 33:
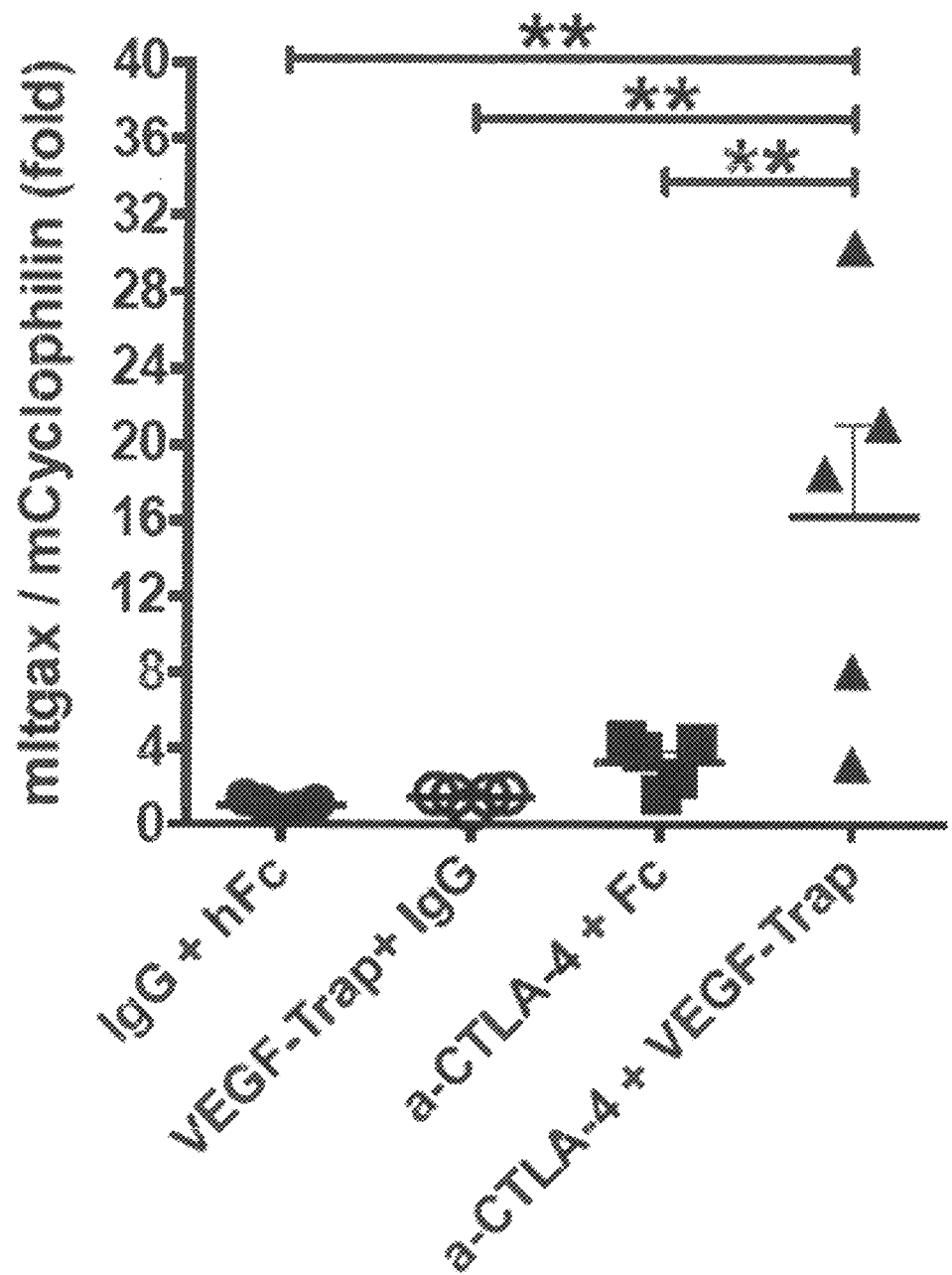

To analyze myeloid cell infiltrates, Itgam (CD11b), Emr1 (F4/80) and Itgax (CD11c) mRNA levels were assessed as markers of myeloid cells, macrophages and dendritic cells, respectively. Anti-CTLA4 antibody or the combination therapy promoted significant increase of myeloid cell infiltrates (FIGS. 31, 32 and 33), with the most prominent increase in dendritic cells infiltration into tumors in the combination group.

In summary, this Example further demonstrates the significant combination effect of anti-CTLA4 antibody and VEGF-Trap against established tumors. Molecular immune profiling of the treated tumors suggests that anti-CTLA4 and VEGF-Trap therapies mediate their effects by regulating immunomodulatory and angiogenic signaling pathways, respectively, both of which may contribute to the improved anti-tumor immune responses in the combination group. Administration of VEGF-Trap revealed activated endothelium and down-regulation of angiogenic factors Dll4, Ang2 and Robo4. Increased expression of E-selectin in the combination group might indicate improved lymphocyte adhesion and rolling, which may result in increased lymphocytes infiltration into the tumor tissues. This result is consistent with increased numbers of T cells and myeloid cells, as well as up-regulation of inflammatory cytokines observed in anti-CTLA-4 treated tumors, and further increased in the combination group, indicating the synergistic nature of anti-tumor immune response to dual VEGF and CTLA-4 blockade.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A pharmaceutical composition, comprising:
   (i) a VEGF antagonist comprising an Ig-like domain 2 of VEGFR1, Ig-like domain 3 of VEGFR2, and a multimerizing domain;
   (ii) an anti-CTLA-4 antibody; and
   (iii) a pharmaceutically acceptable carrier or diluent.

2. The pharmaceutical composition of claim 1, wherein the VEGF antagonist-comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2.

3. The pharmaceutical composition of claim 2, wherein the VEGF Trap comprises VEGFR1R2-FcΔC1(a) encoded by the nucleic acid sequence of SEQ ID NO:1.

4. The pharmaceutical composition of claim 1, wherein the anti-CTLA-4 antibody is an antagonist antibody.

5. The pharmaceutical composition of claim 4, wherein the anti-CTLA-4 antibody is selected from the group consisting of ipilimumab and tremelimumab.

6. The pharmaceutical composition of claim 4, wherein the anti-CTLA-4 antibody has an Fc isotype that provides ADCC and CDC effector activity.

7. The pharmaceutical composition of claim 6, wherein the anti-CTLA-4 antibody is of the IgG1 isotype.

8. The pharmaceutical composition of claim 4, wherein the anti-CTLA-4 antibody has an Fc isotype that provides ADCC and CDC effector activity.

9. The pharmaceutical composition of claim 4, wherein the anti-CTLA-4 antibody is of the IgG1 isotype.

10. A method for extending or prolonging the survival of a subject afflicted with a tumor, the method comprising:
    administering to the subject a therapeutically effective amount of a VEGF antagonist and a therapeutically effective amount of an anti-CTLA-4 antibody.
    wherein the VEGF antagonist is a VEGF Trap comprising Ig-like domain 2 of VEGFR1, Ig-like domain 3 of VEGFR2, and a multimerizing domain.

11. The method of claim 10, wherein the VEGF antagonist and the anti-CTLA-4 antibody are administered to the subject in separate dosage forms.

12. The method of claim 11, wherein the separate dosage forms are administered to the subject simultaneously.

13. The method of claim 11, wherein the separate dosage forms are administered to the subject sequentially.

14. The method of claim 10, wherein the VEGF antagonist and the anti-CTLA-4 antibody are administered to the subject in a single dosage form.

15. The method of claim 10, wherein the VEGF antagonist is administered to the subject intravenously or subcutaneously.

16. The method of claim 10, wherein the anti-CTLA-4 antibody is administered to the subject intravenously or subcutaneously.

17. The method of claim 10, wherein the VEGF Trap comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2.

18. The method of claim 17, wherein the VEGF Trap comprises VEGFR1R2-FcΔC1 (a) encoded by the nucleic acid sequence of SEQ ID NO:1.

19. The method of claim 10, wherein the anti-CTLA-4 antibody is an antagonist antibody.

20. The method of claim 19, wherein the anti-CTLA-4 antibody is selected from the group consisting of ipilimumab and tremelimumab.

21. A method for inducing tumor immunity in a subject, the method comprising:
    administering to the subject a therapeutically effective amount of a VEGF antagonist and a therapeutically effective amount of an anti-CTLA-4 antibody
    wherein the VEGF antagonist is a VEGF Trap comprising Ig-like domain 2 of VEGFR1, Ig-like domain 3 of VEGFR2, and a multimerizing domain.

22. The method of claim 21, wherein the subject is afflicted with a tumor prior to administration of the VEGF antagonist and anti-CTLA-4 antibody to the subject.

23. The method of claim 21, wherein the VEGF antagonist and the anti-CTLA-4 antibody are administered to the subject in separate dosage forms.

24. The method of claim 23, wherein the separate dosage forms are administered to the subject simultaneously.

25. The method of claim 23, wherein the separate dosage forms are administered to the subject sequentially.

26. The method of claim 21, wherein the VEGF antagonist and the anti-CTLA-4 antibody are administered to the subject in a single dosage form.

27. The method of claim 21, wherein the VEGF antagonist is administered to the subject intravenously or subcutaneously.

28. The method of claim 21, wherein the anti-CTLA-4 antibody is administered to the subject intravenously or subcutaneously.

29. The method of claim 21, wherein the VEGF Trap comprises (1) a VEGFR1 component comprising amino acids 27 to 129 of SEQ ID NO:2; (2) a VEGFR2 component comprising amino acids 130-231 of SEQ ID NO:2; and (3) a multimerization component comprising amino acids 232-457 of SEQ ID NO:2.

30. The method of claim 29, wherein the VEGF Trap comprises VEGFR1R2-FcΔC1 (a) encoded by the nucleic acid sequence of SEQ ID NO:1.

31. The method of claim 21, wherein the anti-CTLA-4 antibody is an antagonist antibody.

32. The method of claim 21, wherein the anti-CTLA-4 antibody is selected from the group consisting of ipilimumab and tremelimumab.

* * * * *

SEQUENCE LISTING

```
<160> NUMBER OF SEQ ID NOS: 3

<210> SEQ ID NO 1
<211> LENGTH: 1377
<212> TYPE: DNA
<213> ORGANISM: Artificial Sequence
<220> FEATURE:
<223> OTHER INFORMATION: synthetic

<400> SEQUENCE: 1
atggtcagct actgggacac cggggtcctg ctgtgcgcgc tgctcagctg tctgcttctc      60
acaggatcta gttccggaag tgataccggt agaccttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaatacccc ttcttcgaag catcagcata agaaacttgt aaaccgagac     540
ctaaaaaccc agtctgggag tgagatgaag aaattttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
```

```
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aagggcagc cccgagaacc acaggtgtac    1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

<210> SEQ ID NO 2
<211> LENGTH: 458
<212> TYPE: PRT
<213> ORGANISM: Artificial Sequence
<220> FEATURE:
<223> OTHER INFORMATION: synthetic

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
```

```
                    245                 250                 255
Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
        340                 345                 350

Gln Pro Arg Glu Pro Gln Val Tyr Thr Leu Pro Pro Ser Arg Asp Glu
    355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
        420                 425                 430

Val Phe Ser Cys Ser Val Met His Glu Ala Leu His Asn His Tyr Thr
    435                 440                 445

Gln Lys Ser Leu Ser Leu Ser Pro Gly Lys
450                 455

<210> SEQ ID NO 3
<211> LENGTH: 137
<212> TYPE: PRT
<213> ORGANISM: Artificial Sequence
<220> FEATURE:
<223> OTHER INFORMATION: synthetic

<400> SEQUENCE: 3

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
            85                  90                  95

Met Tyr Pro Pro Pro Tyr Tyr Leu Gly Ile Gly Asn Gly Thr Gln Ile
        100                 105                 110

Tyr Val Ile Ala Lys Glu Lys Lys Pro Ser Tyr Asn Arg Gly Leu Cys
    115                 120                 125

Glu Asn Ala Pro Asn Arg Ala Arg Met
130                 135
```